(12) United States Patent
Zabrecky

(10) Patent No.: US 7,078,064 B2
(45) Date of Patent: Jul. 18, 2006

(54) COMPOSITIONS AND METHODS USEFUL FOR TREATING AND PREVENTING CHRONIC LIVER DISEASE, CHRONIC HCV INFECTION AND NON-ALCOHOLIC STEATOHEPATITIS

(76) Inventor: George Zabrecky, 31 Bailey Ave., Ridgefield, CT (US) 06877

( * ) Notice: Subject to any disclaimer, the term of this patent is extended or adjusted under 35 U.S.C. 154(b) by 131 days.

(21) Appl. No.: 10/726,824

(22) Filed: Dec. 3, 2003

(65) Prior Publication Data

US 2005/0123628 A1    Jun. 9, 2005

(51) Int. Cl.
*A61K 35/78* (2006.01)
(52) U.S. Cl. ................. 424/757; 424/725; 424/777; 514/893; 514/894
(58) Field of Classification Search ................ 424/725, 424/757, 777; 514/893, 894
See application file for complete search history.

(56) References Cited

U.S. PATENT DOCUMENTS 5,770,217 A * 6/1998 Kutilek et al. ............... 424/442
6,455,078 B1 * 9/2002 Wu ............................. 424/725

OTHER PUBLICATIONS

Abe Y. et al. Effectiveness of interferon, glycyrrhizin combination therapy in patients with chronic hepatitis C. *Nippon Rinsho*. 1994; 52(7):1817-22 (in Japanese with English Abstract).

Arase Y. et al. The long term efficacy of glycyrrhizin in chronic hepatitis C patients. *Cancer* 1997; 79(8):1494-500.

Barbaro G. et al Hepatic glutathione deficiency in chronic hepatitis C: quantitative evaluation in patients who are HIV positive and HIV negative and correlations with plasmatic and lymphocytic concentrations and with the activity of the liver disease. *Am J Gastroenterol*. 1996; 91(12):2569-73.

Berkson B.M. A conservative triple antioxidant approach to the treatment of hepatitis C. Combination of alpha lipoic acid (thioctic acid), silymarin, and selenium: three case histories. *Med Klin*. 1999; 94 Suppl 3:84-9.

Boigk G. et al. Silymarin retards collagen accumulation in early and advanced biliary fibrosis secondary to complete bile duct obliteration in rats. *Hepatology* 1997; 26(3):643-649.

Boya P. et al. Antioxidant status and glutathione metabolism in peripheral blood mononuclear cells from patients with chronic hepatitis C. *J Hepatol*. 1999; 31(5):808-14.

Bustamante J. et al., Alpha-lipoic acid in liver metabolism and disease. *Free Radic Biol Med*. 1998; 24(6):1023-39.

Buzzelli G. et al. A pilot study on the liver protective effect of silybin phosphatidylcholine complex (IdB1016) in chronic active hepatitis. *Int J Clin Pharmacol Ther Toxicol*. 1993; 31:456-460.

Chrobot A.M. et al. Antioxidant defense in children with chronic viral hepatitis B and C. *Med Sci Monit* 2000; 6(4): 713-8.

Cook G.C. et al. Results of a controlled clinical trial of glutathione in cases of hepatic cirrhosis. *Gut* 1965; 6(5):472-6.

Dehmlow C. et al. Inhibition of Kupffer cell functions as an explanation for the hepatoprotective properties of silibinin. *Hepatology* 1996; 23:749-754.

Eberhardt G. et al. Controlled study of the therapeutic effect of B vitamins and an anabolic steroid in chronic hepatitis. *Disch Med Wochenschr*. 1975; 100(41):2074-82 (in German with English abstract).

Feher I. et al. Liver-protective action of silymarin therapy in chronic alcoholic liver diseases. *Orv Hetil*. 1989; 130:2723-2727 (in Hungarian with English abstract).

Ferenci P. et al., Randomized controlled trial of silymarin treatment in patients with cirrhosis of the liver. *J Hepatol*. 1989; 9:105-113.

(Continued)

*Primary Examiner*—Christopher R. Tate
(74) *Attorney, Agent, or Firm*—Jones Day

(57) ABSTRACT

The invention relates generally to compositions comprising antioxidants useful for reducing oxidative stress and lipid peroxidation, and treating chronic liver disease, chronic hepatitis C virus infection and non-alcoholic steatohepatitis. In particular, the invention relates to the preparation and oral administration of compositions comprising glycyrrhizin, *schisandra*, ascorbic acid, L-glutathione, silymarin, lipoic acid, and d-alpha-tocopherol. The invention also relates to the preparation and parenteral administration of compositions comprising glycyrrhizin, ascorbic acid, L-glutathione, and vitamin B-complex, preferably by infusion or intravenous injection. The invention further relates to methods of using the antioxidants, oral compositions and parenteral compositions.

52 Claims, 8 Drawing Sheets

OTHER PUBLICATIONS

Fujisawa Y. et al. Glycyrrhizin inhibits the lytic pathway of complement—possible mechanism of its anti-inflammatory effect on liver cells in viral hepatitis. *Microbiol Immunol.* 2000; 44(9):799-804.

Gagliardi B. et al., Results of a double blind study on the effect of silymarin in the treatment of acute viral hepatitis, carried out at two medical centers. *Med Klin.* 1978; 73:1060-1065.

Gut J. et al. Mechanisms of halothane toxicity: novel insights. *Pharmacol Ther.* 1993; 58(2): 133-55.

Hargreaves R.J. et al. Studies on the effects of L-ascorbic acid on acetaminophen-induced hepatotoxicity. II. An *in vivo* assessment in mice of the protection afforded by various dosage forms of ascorbate. *Toxicol Appl Pharmacol.* 1982; 64(3):380-92.

Hill D.B. et al. Antioxidants attenuate nuclear factor-kappa B activation and tumor necrosis factor-alpha production in alcoholic hepatitis patient monocytes and rat Kupffer cells, in vitro. *Clin Biochem.* 1999; 32(7):563-70.

Houglum K. et al. A pilot study of the effects of d-alpha-tocopherol on hepatic stellate cell activation in chronic hepatitis C. *Gastroenterology* 1997; 113(4): 1069-73.

Hruby K. et al. Chemotherapy of Amanita phalloides poisoning with intravenous silibinin. *Hum Toxicol.* 1983; 2:183-195.

Iimuro Y. et al. The glutathione precursor L-2-oxothiazolidine-4-carboxylic acid protects against liver injury due to chronic enteral ethanol exposure in the rat. *Hepatology* 2000; 31(2): 391-8.

Iino S. et al. Therapeutic effects of stronger neo-minophagen C at different doses on chronic hepatitis and liver cirrhosis. *Hepatol Res.* 2001; 19(1):31-40.

Kang S.Y. et al. Hepatoprotective activity of scopoletin, a constituent of Solarium lyratum. *Arch Pharm Res.* 1998; 21(6): 718-22.

Khodykin A.V. The efficacy of a diet enriched by lipotropic factors, and vitamin C and vitamin B-complex in patients with chronic hepatitis. *Vopr Pitan.* 1958; 17(2):19-29 (in Russian with English summary).

Komar VI. Application of vitamin B12 in combined treatment of viral hepatitis. *Vopr Pitan.* 1982; (1):26-9 (in Russian with English summary).

Li X.J., Scavenging effects on active oxygen radicals by schizandrins with different structures and configurations. *Free Radic Biol Med.* 1990; 9(2):99-104.

Liu G.T. Pharmacological actions and clinical use of fructus schizandrae. *Chin Med J. (Engl)* 1989;102(10):740-9.

Liu K.T., Pharmacological properties of Dibenzo[a,c-]cyclooctene derivatives isolated from Fructus Schisandra Chinensis III. Inhibitory effects on carbon tetrachloride-induced lipid peroxidation, metabolism and covalent binding of carbon tetrachloride to lipids. *Chem Biol Interact.* 1982; 41(1):39-47.

Liu S.L. et al. Vitamin E therapy of acute CC14-induced hepatic injury in mice is associated with inhibition of nuclear factor kappa B binding. *Hepatology* 1995; 22(5):1474-81.

Loguercio C. et al. Alpha-glutathione transferases in HCV-related chronic hepatitis: a new predictive index of response to interferon therapy? *J Hepatol.* 1998; 28(3):390-5.

Look M.P. et al. Interferon/antioxidant combination therapy for chronic hepatitis C—a controlled pilot trial. *Antiviral Res.* 1999; 43(2):113-22.

Lu H. et al., Effect of dibenzo[a,c]cyclooctene lignans isolated from *Fructus schizandrae* on lipid peroxidation and anti-oxidative enzyme activity. *Chem Biol Interact.* 1991; 78(1):77-84.

Luper S. A review of plants used in the treatment of liver disease: Part 1. *Altern Med Rev.* 1998; 3:410-421.

Magliulo E. et al. Results of a double blind study on the effect of silymarin in the treatment of acute viral hepatitis, carried out at two medical centres. *Med Klin.* Jul. 14, 1978; 73(28-29): 1060-5 (in German with English summary).

Mahmood S. et al. Effect of vitamin E on serum aminotransferase and thioredoxin levels in patients with viral hepatitis C. *Free Radic Res.* 2003; 37(7):781-5.

Marshall A.W. et al. Treatment of alcohol-related liver disease with thioctic acid: a six month randomized double-blind trial. *Gut* 1982; 23(12):1088-93.

Matsuo K. et al. Lamivudine and glycyrrhizin for treatment of chemotherapy-induced hepatitis B virus (HBV) hepatitis in a chronic HBV carrier with non-Hodgkin lymphoma. *Leuk Lymphoma* 2001; 41(1-2): 191-5.

McPartland J.M. Viral hepatitis treated with *Phyllanthus amarus* and milk thistle (*Silybum marianum*). *Complementary Medicine International* 1996; Mar./Apr.: 40-42.

Meydani S.N. et al. Vitamin E supplementation and in vivo immune response in healthy elderly subjects. A randomized controlled trial. *JAMA* 1997; 277(17): 1380-6.

Mitra A. et al. Effect of ascorbic acid esters on hepatic glutathione levels in mice treated with a hepatotoxic dose of acetaminophen. *J Biochem Toxicol.* 1991; 6(2):93-100.

Moller E. et al. A contribution to the treatment of chronic liver diseases *Med Klin.* 1976; 71(43):1831-5.

Morazzoni P. et al., Comparative pharmacokinetics of silipide and silymarin in rats. *Eur J Drug Metab Pharmacokinet.* 1993; 18:289-297.

Moscarella S. et al., Therapeutic and antilipoperoxidant effects of silybin-phosphatidylcholine complex in chronic liver disease: preliminary results. *Curr Ther Res.* 1993; 53:98-102.

Nagita A. et al. Assessment of hepatic vitamin E status in adult patients with liver disease. *Hepatology* 1997; 26(2):392-7.

Nakashima T. et al. Thioredoxin levels in the sera of untreated viral hepatitis patients and those treated with glycyrrhizin or ursodeoxycholic acid. *Antioxid Redox Signal.* 2000 Winter; 2(4):687-94.

Numazaki K. et al. Effect of glycyrrhizin in children with liver dysfunction associated with cytomegalovirus infection. *Tohoku J Exp Med.* 1994; 172(2):147-53.

Okamoto T. The protective effect of glycyrrhizin on anti-Fas antibody-induced hepatitis in mice. *Eur J Pharmacol.* 2000; 387(2):229-32.

Okamoto T. et al Glycyrrhizin protects mice from concanavalin A-induced hepatitis without affecting cytokine expression. *Int J Mol Med.* 1999; 4(2):149-52.

Patrick L. Hepatitis C: epidemiology and review of complementary/alternative medicine treatments. *Altern Med Rev.* 1999; 4(4):220-38.

Pauling L. Vitamin C prophylaxis for posttransfusion hepatitis. *Am J Clin Nutr.* 1981; 34(9):1978-80.

Rambousek V. et al. Severe Amanita phalloides poisoning in a 7-year-old girl. *Cesk Pediatr.* 1993; 48:332-333 (in Czech with English summary).

Ravindranath V. et al. Effect of modulators of glutathione synthesis on the hepatotoxicity of 2-methylfuran. *Biochem Pharmacol* 1991; 41(9): 1311-8.

Rocchi E. et al. Antioxidant liposoluble vitamins and carotenoids in chronic hepatitis. 2001; 12(2):116-121.

Sabeel A.I. et al. Intensive hemodialysis and hemoperfusion treatment of Amanita mushroom poisoning. *Mycopathologia* 1995; 131:107-114.

Salmi H.A. et al. Effect of silymarin on chemical, functional, and morphological alterations of the liver; A double blind controlled study. *Scand J Gastroenterol*. 1982; 17:517-521.

Schalm S.W. et al. New treatment strategies in non-responder patients with chronic hepatitis C. *J Hepatol*. 1999; 31 Suppl 1:184-8.

Shibata S. A drug over the millennia: pharmacognosy, chemistry, and pharmacology of licorice. *Yakugaku Zasshi* 2000; 120(10): 849-62.

Sinclair S. Chinese herbs: a clinical review of Astragalus, Ligusticum, and Schizandrae. *Altern Med Rev*. 1998; 3(5): 338-44.

Speck R.F. et al. Prednisolone stimulates hepatic glutathione synthesis in mice. Protection by prednisolone against acetaminophen hepatotoxicity in vivo. *J Hepatol*. 1993; 18(1):62-7.

Sun F. et al. Evaluation of oxidative stress based on lipid hydroperoxide, vitamin C and vitamin E during apoptosis and necrosis caused by thioacetamide in rat liver. *Biochem Biophys Acta*. 2000; 1500(2):181-5.

Sun F. et al. Evaluation of oxidative stress during apoptosis and necrosis caused by carbon tetrachloride in rat liver. *Biochim Biophys Acta*. 2001;1535(2):186-91.

Swietek K. et al. Reduced glutathione concentration in erythrocytes of patients with acute and chronic viral hepatitis. *J Viral Hepatol*. 1997; 4:139-41.

Takyar S.S. et al. Vitamin B12 stalls the 80 S ribosomal complex on the hepatitis C internal ribosome entry site. *J Mol Biol*. 2002; 319(1):1-8.

Tandon A. et al. Treatment of subacute hepatitis with Lamivudine and intravenous Glycyrrhizin: a pilot study. *Hepatol Res*. 2001; 20(1): 1-8.

Tanyalcin T. et al.The effects of chronic hepatitis C and B virus infections on liver reduced and oxidized glutathione concentrations. *Hepatol Res*. 2000; 18(2):104-109.

Tsubota A. et al. Combined ursodeoxycholic acid and glycyrrhzin therapy for chronic hepatitis C virus infection: a randomized controlled trial in 170 patients. *Eur J Gastroenterol Hepatol*. 1999; 11(10):1077-83.

Valenzuela A. et al. Biochemical bases of the pharmacological action of the flavonoid silymarin and of its structural isomer silibinin. *Biol Res*. 1994; 27(2):105-12.

Vailati A. et al. Randomized open study of the dose-effect relationship of a short course of IdB 1016 in patients with viral or alcoholic hepatitis. *Fitoterapia* 1993; 64:219-228.

van Rossum T.G. et al. Pharmacokinetics of intravenous glycyrrhizin after single and multiple doses in patients with chronic hepatitis C infection. *Clin Ther*. 1999; 21(12):2080-90.

van Rossum T.G. et al. Intravenous glycyrrhizin for the treatment of chronic hepatitis C: a double-blind, randomized, placebo-controlled phase I/II trial. *J Gastroenterol Hepatol*. 1999; 14(11):1093-1099.

van Rossum T.G. et al. Review article: glycyrrhizin as a potential treatment for chronic hepatitis C. *Aliment Pharmacol Ther*. 1998; 12(3):199-205.

Vendermiale G. et al. Oxidative stress in symptom-free HCV carriers: relation with ALT flare-up. *Eur J Clin Invest*. 2001; 31(1):54-63.

Vogel G. et al. Protection by silibinin against Amanita phalloides intoxication in beagles. *Toxicol Appl Pharmacol*. 1984; 73:355-362.

von Herbay A. et al. Vitamin E improves the aminotransferase status of patients suffering from viral hepatitis C: a randomized, double-blind, placebo-controlled study. *Free Radic Res*. 1997; 27(6):599-605.

von Herbay A. et al. Diminished plasma levels of vitamin E in patients with severe viral hepatitis. *Free Radic Res*. 1996; 25(6):461-6.

Yamashiki M. et al. Effects of the Japanese herbal medicine "Sho-saiko-to" (TJ-9) on *in vitro* interleukin-10 production by peripheral blood mononuclear cells of patients with chronic hepatitis C. *Hepatology* 1997; 25(6):1390-7.

Yoshikawa M. et al. Mechanisms of Hepatocellular Injury: Effects of Glycyrrhizin on Immune-Mediated Cytotoxicity. *J Gastroenterol Hepatol*. 1997; 12(3):243-248.

Younes M. et al. Protection by exogenous glutathione against hypoxic and cyanide-induced damage to isolated perfused rat livers. *Toxicol Lett*. 1990; 50(2-3):229-36.

* cited by examiner

SCORING & GRADING SYSTEMS

Table 1. HAI for numerical scoring of liver biopsy specimens

| I. Periportal +/– Bridging Necrosis | Score | II. Intralobular Degeneration* and Focal Necrosis | Score | III. Portal Inflammation | Score | IV. Fibrosis | Score |
|---|---|---|---|---|---|---|---|
| A. None | 0 | A. None | 0 | A. No portal inflammation | 0 | A. No fibrosis | 0 |
| B. Mild piecemeal necrosis | 1 | B. Mild (acidophilic bodies, ballooning degeneration and/or scattered foci of hepatocellular necrosis in <1/3 of lobules or nodulles) | 1 | B. Mild (sprinkling of inflammatory cells in <1/3 of portal tracts) | 1 | B. Fibrous portal expansion | 1 |
| C. Moderate piecemeal necrosis (involves *less* than 50% of the circumference of most portal tracts) | 3 | C. Moderate (involvement of 1/3-2/3 of lobules or nodules) | 3 | C. Moderate (increased inflammatory cells in 1/3-2/3 of portal tracts) | 3 | C. Bridging fibrosis (portal-portal or portal-central linkage) | 3 |
| D. Marked piecemeal necrosis (involves *more* than 50% of the circumference of most portal tracts) | 4 | D. Marked (involvement of >2/3 of lobules or nodules) | 4 | D. Marked (dense packing of inflammatory cells in >2/3 of portal tracts) | 4 | D. Cirrhosis† | 4 |
| E. Moderate piecemeal necrosis *plus* bridging necrosis‡ | 5 | | | | | | |
| F. Marked piecemeal necrosis *plus* bridging necrosis‡ | 6 | | | | | | |
| G. Multilobular necrosis§ | 10 | | | | | | |

COMPOSITIONS AND METHODS USEFUL FOR TREATING AND PREVENTING CHRONIC LIVER DISEASE, CHRONIC HCV INFECTION AND NON-ALCOHOLIC STEATOHEPATITIS

1. FIELD OF THE INVENTION

The invention relates generally to compositions comprising antioxidants useful for reducing oxidative stress and/or lipid peroxidation, and for treating and/or preventing chronic liver disease, chronic hepatitis C virus infection, and/or non-alcoholic steatohepatitis. In particular, the invention relates to oral compositions and parenteral compositions comprising one or more, or all of the antioxidants glycyrrhizin, *schisandra* extract, ascorbic acid, glutathione, silymarin, lipoic acid, d-alpha-tocopherol, and vitamin B-complex. The invention also relates to methods of using one or more of the antioxidants, the oral compositions and/or parenteral compositions to reduce oxidative stress and/or lipid peroxidation, and/or to treat and/or prevent chronic liver disease, chronic hepatitis C virus infection, and/or non-alcoholic steatohepatitis in a subject. The invention further relates to methods of making the antioxidants and compositions as well as methods of administering the antioxidants and compositions.

2. BACKGROUND OF THE INVENTION

2.1 Chronic Liver Disease

Chronic liver disease is marked by the gradual destruction of liver tissue over time. Several liver diseases fall under this category, including cirrhosis and fibrosis (often the forerunner of cirrhosis) of the liver.

Cirrhosis is the seventh leading cause of death in the United States, according to the National Institute of Diabetes and Digestive and Kidney Diseases (NIDDK). Cirrhosis is defined pathologically by the loss of normal microscopic lobular architecture with fibrosis (i.e., the growth of scar tissue due to infection, inflammation, injury, or even healing) and nodular regeneration. Because of chronic damage to the liver, scar tissue slowly replaces normal functioning liver tissue resulting in progressively diminishing blood flow through the liver. As the normal liver tissue is lost, nutrients, hormones, drugs and poisons are not processed effectively by the liver. In addition, protein production and other substances produced by the liver are inhibited.

Symptoms of cirrhosis vary, depending on severity and individuals. Symptoms may include abnormal nerve function, ascites (build-up of fluid in the abdominal cavity), breast enlargement in men, coughing up or vomiting blood, curling of fingers (Dupuytren contracture of the palms), gallstones, hair loss, itching, jaundice, kidney failure, liver encephalopathy, muscle loss, poor appetite, portal hypertension, redness of palms, salivary gland enlargement in cheeks, shrinking of testes, small spider-like veins in skin, weakness, weight loss, etc. The symptoms of cirrhosis may resemble other conditions or medical problems. Mild cirrhosis may not exhibit any symptoms at all.

The most common cause of cirrhosis is alcohol abuse. Other causes include hepatitis and other viruses (e.g., HCV as described in Section 2.2 infra.), use of certain drugs, chemical exposure, bile duct obstruction, autoimmune diseases, obstruction of outflow of blood from the liver (i.e., Budd-Chiari syndrome), heart and blood vessel disturbances, alpha1-antitrypsin deficiency, high blood galactose levels, high blood tyrosine levels, glycogen storage disease, diabetes, malnutrition, hereditary accumulation of too much copper (Wilson Disease) or iron (hemochromatosis).

Clinical signs of chronic liver disease include spider angiomas (a central arteriole from which numerous small branching vessels radiate), jaundice (yellowish discoloration of the skin), pruritus (itching), gynecomastia (enlargement of the male breast), ascites (an effusion and accumulation of serous fluid in the abdominal cavity), encephalopathy, asterixis (flapping tremor), etc. In addition to a complete medical history and medical examination, diagnostic procedures for cirrhosis may include specific laboratory tests, liver function tests, liver biopsy, and cholangiography (x-rays of the bile ducts).

Cirrhosis is a progressive liver disease, and the damage sustained by the liver is irreversible. However, with proper nutrition, avoidance of certain toxins (i.e., alcohol), vitamin supplementation, and management of cirrhosis complications, further liver damage can often be delayed or stopped. In severe cases of cirrhosis, liver transplantation may be considered.

2.2 Hepatitis C Virus Infection

The hepatitis C virus (HCV) is a blood-borne virus. HCV infection continues to be a major health problem in the U.S. and worldwide. According to the National Health and Nutrition Examination Survey (NHANES) of 1988–1994, 3.9 million Americans have been infected with hepatitis C virus, and of this group, 2.7 million were estimated to have chronic HCV infection. An estimated 50,000 cases occur annually in the U.S., making HCV infection the most common blood-borne infection in the U.S. (Wesley A. et al. Epidemiology of hepatitis C: geographic differences and temporal trends. *Semin Liver Dis.* 2000; 20(1):1–16). The exact prevalence of the disease is unknown, however, in Western Europe it is estimated to be 1% of the general population, 5% in some parts of Eastern Europe, and 10% in Egypt (Alberti A. et al. Natural history of hepatitis C. *J Hepatol.* 1999; 31 Suppl 1:17–24). The prevalence in IV drug users is as high as 58–84% (Schwimmer J. B. et al. Transmission, natural history, and treatment of hepatitis C virus infection. *Semin Liver Dis.* 2000; 20(1): 37–46), putting them at high risk.

HCV is a single stranded RNA virus of the Flaviviridae family. There are 6 HCV genotypes (1a, 1b, 2a, 2b, 3, 4, 5, and 6) and more than 50 subtypes. These genotypes differ by as much as 30–50% in their nucleotide sequences. The virus has a high propensity to mutate, which further adds to the difficulties in vaccine development and treatment efficacy.

The hepatitis C virus enters the body through direct blood exposure. The virus attacks cells in the liver, where it multiplies (replicates) and therefore, causes liver inflammation and kills liver cells. Regardless of mode of acquisition, as many as 50–70% of people initially infected with HCV become chronically infected (the infection does not clear up within six months), and more than 50% of the HCV-infected people will develop chronic liver disease. Most people with chronic HCV infection do not have symptoms and lead normal lives. However, in 10–25% of people with chronic HCV infection, the disease progresses over decades, and may lead to serious liver damage, cirrhosis, and/or liver cancer. The prevalence of cirrhosis, which is pathologically characterized by loss of the normal microscopic lobular architecture, with fibrosis and nodular regeneration, is above 50% in these patients. Today, HCV infection is the leading cause for liver transplants.

The current understanding of the liver pathology in chronic HCV-infected patients is that the damage is due to the host immune response and not to the virus itself. Several lines of evidence support the concept that HCV, similar to HBV, is a non-cytopathic virus in the majority of cases (Rehermann B. Cellular immune response to the hepatitis C virus. *J Viral Hepatol.* 1999; 6 Suppl 1:31–5; Nelson D. R. et al. Pathogenesis of chronic hepatitis C virus infection. *Antivir Ther.* 1998; 3 (Suppl 3):25–35; Rehermann B. et al. Cell mediated immune response to the hepatitis C virus. *Curr Top Microbiol Immunol.* 2000; 242:299–325). A heightened host CD8+ cytotoxic T lymphocyte (CTL) response and an elevated cytokine tumor necrosis factor alpha (TNF-a) level, which are important in limiting viral replication, become the same immune responses responsible for damage to the liver once the infection has become chronic (Takaki A. et al. Cellular immune responses persist and humoral responses decrease two decades after recovery from a single-source outbreak of hepatitis C. *Nat Med.* 2000; 6(5):578–82). A significant correlation has also been found to exist between the number of lobular CD8+ cells and liver enzymes levels, suggesting the prominent role of T-cell mediated cytotoxicity in the genesis of hepatocellular damage (Rehermann B., supra. (1999); Nelson D. R. et al. supra.; Rehermann B. et al. supra. (2000); Naoumov N. V. Hepatitis C virus-specific CD4 (+) T cells: do they help or damage? *Gastroenterology.* 1999; 117(4):1012–4; Gerlach J. T. et al. Recurrence of hepatitis C virus after loss of virus-specific CD4 (+) T-cell response in acute hepatitis C. *Gastroenterology.* 1999; 117(4):933–41; Lohr H. F. et al. The viral clearance in interferon-treated chronic hepatitis C is associated with increased cytotoxic T cell frequencies. *J Hepatol.* 1999; 31(3):407–15).

There is currently no vaccine or cure for HCV infection. Current treatments are either based on anti-viral drugs or focus on attempts to augment the anti-viral immune response. However, the results of these approaches have been largely disappointing. The current response rate to the combination therapy of interferon and ribavirin is less than 50%. The vast majority of treated patients are either non-respondents or will suffer from relapse of the disease following termination of treatment. Moreover, these treatments are associated with a high percentage of side effects.

2.3 Non-Alcoholic Steatohepatitis

Non-alcoholic steatohepatitis (NASH), also known as non-alcoholic fatty liver disease, describes a hepatic disorder typically characterized by an alcoholic pathogenesis without alcohol consumption (Blechacz B. et al. NASH—nonalcoholic steatohepatitis [in German]. *Z Gastroenterol.* 2003;41(1):77–90). The fat deposit in liver cells is mostly triglyceride, and the severity of NASH is directly related to the amount of fat in the liver. Histologically, if 50% of liver cells had steatosis (fatty liver accumulation), or if the total weight of fat is greater than 5% of the entire liver, then steatohepatitis can be diagnosed. NASH is further characterized by elevated serum aminotransferase activities with hepatic steatosis, inflammation, and occasionally fibrosis that may progress to cirrhosis.

The prevalence of NASH is 3–19% throughout most of the world. There are many possible causes of NASH but there isn't a definite source. The most likely causes are obesity from poor diet, diabetes, long-term use of steroids and use of tetracycline (Bacon B. R. et al. Nonalcoholic steatohepatitis: An expanded clinical entity. *Gastroenterology* 1994; 107:1103–91; Powell E. E. et al. The natural history of nonalcoholic steatohepatitis: a follow-up study of forty-two patients for up to 21 years. *Hepatology* 1990; 11:74–80). Some studies have shown sign of steatosis reversal after weight loss (Eriksson S. et al. Nonalcoholic steatohepatitis in obesity: A reversible condition. *Acta Med Scand.* 1986; 220:83–8; Sheth S. G. et al. Nonalcoholic steatohepatitis. *Ann Intern Med.* 1997; 126(2):137–45).

There is currently no established treatment that exists for this potentially serious disorder. Treatment of patients with nonalcoholic fatty liver has typically been focused on the management of associated conditions such as obesity, diabetes mellitus, and hyperlipidemia as well as discontinuation of potentially hepatotoxic drugs (Angulo P. et al. Treatment of nonalcoholic fatty liver: Present and emerging therapies. *Sem Liver Dis.* 2001;21(1):81–88).

2.4 Oxidative Stress and Lipid Peroxidation

Oxygen is the primary oxidant in metabolic reactions designed to obtain energy from the oxidation of a variety of organic molecules. Oxidative stress is a disturbance in the balance between the production of reactive oxygen species (ROS) and antioxidant defenses resulting in abnormally high levels of ROS (Klaunig J. E. et al. The role of oxidative stress in chemical carcinogenesis. *Environ Health Perspect.* 1998;106 Suppl 1:289–95). Mitochondria are the main source of ROS in the cell. Studies have shown that mitochondrial dysfunction could be a major mechanism of drug-induced liver disease (Pessayre D. et al. Hepatotoxicity due to mitochondrial dysfunction. *Cell Biol Toxicol.* 1999; 15(6):367–73). Oxidative stress, as reflected in blood and urine by a wide range of pro- and antioxidant markers, is a significant feature of hepatitis C virus infection (Jain S. K. et al. Oxidative stress in chronic hepatitis C: not just a feature of late stage disease. *J Hepatol.* 2002; 36(6):805–11).

Most aerobes can tolerate mild oxidative stress, but severe oxidative stress results in damage to DNA, proteins, lipids, and carbohydrates. Lipid peroxidation is initiated by a reaction between ROS and fatty acid side chains of cell membranes. The ROS abstracts a hydrogen atom, forming a fatty acid side chain peroxyl radical, which in turn can attack other fatty acid side chains and propagate lipid peroxidation. The chain reaction continues and lipid peroxides accumulate in the membrane. Lipid peroxidation can have profound effects on cellular function by altering membrane function—increasing fluidity, compromising permeability, and inactivating of membrane-bound receptors and enzymes.

Evidence suggests that oxidative stress and mitochondrial injury play a role in the mechanisms of liver injury in chronic HCV infection (Okuda M. et al. Mitochondrial injury, oxidative stress, and antioxidant gene expression are induced by hepatitis C virus core protein. *Gastroenterology.* 2002;122(2):366–75; Kolen T. et al. Oxidative stress markers in hepatitis C infected hemodialysis patients. *J Nephrol.* 2002;15(3):302–7) and NASH (Yu A. S. et al. Nonalcoholic fatty liver disease. *Rev Gastroenterol Disord.* 2002;2(1): 11–9; Mehta K. et al. Nonalcoholic fatty liver disease: pathogenesis and the role of antioxidants. *Nutr Rev.* 2002; 60(9):289–93). There is accumulating evidence that oxidative stress plays a considerable role in the development of liver fibrosis by acting in different cell types and in different signaling pathways (Gebhardt R. Oxidative stress, plant-derived antioxidants and liver fibrosis. *Planta Med.* 2002; 68(4):289–96). Recent studies have shown that oxidative stress and lipid peroxidation play a major role in the fatty liver accumulation (steatosis) that leads to necroinflammation and necrosis of hepatic cells. Necrosis, both the piecemeal and bridging types, are associated with a poor prognosis in chronic hepatitis. Fatty tissue accumulation in the liver increases the potential for oxidative stress to trigger lipid peroxidation, leading to cytotoxic intermediates that induce inflammation and fibrosis via immunological pathways. Both in alcoholic and non-alcoholic hepatitis, steatosis and the lipid peroxidation that follows can lead to activation of stellate cells, the principal cells in the liver responsible for fibrogenesis and, ultimately, cirrhosis.

It is the goal of the present invention to formulate compositions comprising antioxidants useful for treating oxidative stress and/or lipid peroxidation, especially that associated with chronic liver disease, chronic HCV infection and NASH.

2.5 Antioxidants 2.5.1 Glycyrrhizin

Glycyrrhizin is extracted from the roots of licorice plants (*Glycyrrhiza glabra, Glycyrrhiza uralensis*), which are native to Turkey, Iraq, Spain, Greece, and northern China and is extensively cultivated in Russia, Spain, Persia, and India. Licorice plants have been used for thousands of years for sweetening, flavoring, and for treatment of a variety of health problems such as peptic ulcer, colds and other viral infections, microbial and parasitic infections, and cancers. It is a source of magnesium, silicon and thiamine.

Studies have shown glycyrrhizin to be effective in treating chronic HCV-infected patients who do not respond to interferon therapy (Abe Y. et al. Effectiveness of interferon, glycyrrhizin combination therapy in patients with chronic hepatitis C [in Japanese]. *Nippon Rinsho.* 1994; 52(7): 1817–22). Experimental hepatitis and cirrhosis studies on rats found that glycyrrhizin is useful in completely reversing liver dysfunction by promoting the regeneration of liver cells and at the same time inhibiting fibrosis (Numazaki K. et al. Effect of glycyrrhizin in children with liver dysfunction associated with cytomegalovirus infection. *Tohoku J Exp Med.* 1994; 172(2):147–53). The intravenous administration of glycyrrhizin has been known to decrease elevated plasma transaminase enzymes in patients with chronic viral hepatitis (van Rossum T. G. et al. Intravenous glycyrrhizin for the treatment of chronic hepatitis C: a double-blind, randomized, placebo-controlled phase I/II trial. *J Gastroenterol Hepatol.* 1999; 14(11):1093–1099). This reduction in the levels of transaminase enzymes is mediated partly by the inhibition of immune-mediated cytotoxicity against hepatocytes (Yoshikawa M. et al. Effects of Glycyrrhizin on Immune-Mediated Cytotoxicity. *J Gastroenterol Hepatol.* 1997; 12(3):243–248).

Glycyrrhizin has also been shown to be effective in preventing the development of hepatocellular carcinoma in chronic HCV-infected patients (van Rossum T. G. et al. Review article: glycyrrhizin as a potential treatment for chronic hepatitis C. *Aliment Pharmacol Ther.* 1998; 12(3): 199–205; Arase Y. et al. The long term efficacy of glycyrrhizin in chronic hepatitis C patients. *Cancer* 1997; 79(8): 1494–500). Further, the level of thioredoxin, a thiol-containing protein induced by various oxidative stresses, was significantly higher in HCV-infected patients than in controls but was markedly decreased following treatment with glycyrrhizin (Nakashima T. et al. Thioredoxin levels in the sera of untreated viral hepatitis patients and those treated with glycyrrhizin or ursodeoxycholic acid. *Antiioxid Redox Signal.* 2000 Winter; 2(4):687–94).

2.5.2 schisandra (Wu Wei Zi)

*Schisandra (Schisandra chinensis)* is a woody vine, which is a member of the Magnoliaceae family, with numerous clusters of tiny, bright red berries (Fructus *schisandra*). *Schisandra* is distributed throughout northern and northeast China and the adjacent regions of Russia and Korea. Traditionally, the *schisandra* berries are harvested in the fall, dried, and then ground to be used medicinally. The berries are purported to have sour, sweet, salty, hot, and bitter tastes. This unusual combination of flavors is reflected in *schisandra's* Chinese name "wu-wei-zi", meaning "five taste fruit."

*Schisandra* has been studied for its hepato-protective abilities and functions as a potent antioxidant. Studies have shown that *schisandra* protects liver from lipid peroxidation or injury induced by toxic substances such as carbon tetrachloride (CC14) (Liu K. T., Pharmacological properties of Dibenzo [a, c] cyclooctene derivatives isolated from Fructus *Schisandra* Chinensis III. Inhibitory effects on carbon tetrachloride-induced lipid peroxidation, metabolism and covalent binding of carbon tetrachloride to lipids. *Chem Biol Interact.* 1982; 41(1):39–47). By lowering serum glutamic pyruvic transaminase (SGPT) levels, reducing ethanol induced malondialdehyde (MDA) formation, and increasing superoxide dismutase and catalase activities, *schisandra* and its active components have been found to be effective against viral and chemical induced hepatitis in subjects (Arase et al., supra.; Lu H. et al., Effect of dibenzo [a, c] cyclooctene lignans isolated from Fructus *schisandra* on ADPH induced lipid peroxidation (malondialdehyde (MDA) formation) and anti-oxidative enzyme activity. *Chem Biol Interact.* 1991; 78(1):77–84; Li X. J., Scavenging effects on active oxygen radicals by schizandrins with different structures and configurations. *Free Radic Biol Med.* 1990; 9(2): 99–104).

2.5.3 Ascorbic Acid (Vitamin C)

Ascorbic acid is more commonly known as vitamin C, which is a water-soluble vitamin that has a number of biological functions. Ascorbic acid is derived from glucose via the uronic acid pathway. The enzyme L-gulonolactone oxidase, which is responsible for the conversion of gulonolactone to ascorbic acid, is absent in primates, making ascorbic acid a requirement in the diet of humans.

Vitamin C has been used to treat subjects with chronic hepatitis (Khodykin A. V. The efficacy of a diet enriched with lipotropic factors, vitamin C and vitamin B complex in patients with chronic hepatitis. *Vopr Pitan.* 1958; 17(2): 19–29 (in Russian)). Beneficial effects of vitamin C on plasma glutathione regeneration and hepatotoxicity have also been reported (Hargreaves R. J. et al. Studies on the effects of L-ascorbic acid on acetaminophen-induced hepatotoxicity. II. An in vivo assessment in mice of the protection afforded by various dosage forms of ascorbate. *Toxicol Appl Pharmacol.* 1982; 64(3):380–92; Mitra A. et al. Effect of ascorbic acid esters on hepatic glutathione levels in mice treated with a hepatotoxic dose of acetaminophen. *J Biochem Toxicol.* 1991; 6(2):93–100; Pauling L. Vitamin C prophylaxis for posttransfusion hepatitis. *Am J Clin Nutr.* 1981; 34(9):1978–80).

2.5.4 Glutathione

Glutathione is a sulfhydryl (—SH) antioxidant, antitoxin, and enzyme cofactor that naturally occurs in cells. Glutathione is primarily synthesized in the liver and is involved in DNA synthesis and repair, protein and prostaglandin synthesis, amino acid transport, metabolism of toxins and carcinogens, immune system function, prevention of oxidative cell damage, and enzyme activation.

Glutathione is a powerful antioxidant. It recycles other well-known antioxidants such as vitamin C and vitamin E, keeping them in active state. In addition, glutathione is an important detoxifying agent that is found in high levels at the liver, kidneys, and lungs. Pretreatment with glutathione inhibits tumor necrosis factor-alpha (TNF-a) activity in alcoholic hepatitis (AH) (Hill D. B. et al. Antioxidants attenuate nuclear factor-kappa B activation and tumor necrosis factor-alpha production in alcoholic hepatitis patient monocytes and rat Kupffer cells, in vitro. *Clin Biochem.*

1999; 32(7):563–70). The protective effects of glutathione against hypoxic and cyanide-induced hepatotoxicity substantiate the role of oxidative stress in both types of injury (Younes M. et al. Protection by exogenous glutathione against hypoxic and cyanide-induced damage to isolated perfused rat livers. *Toxicol Lett.* 1990; 50(2–3):229–36). However, some earlier studies have shown that in individuals with cirrhosis, oral glutathione has no effect on liver function tests (Cook G. C. et al. Results of a controlled clinical trial of glutathione in cases of hepatic cirrhosis. *Gut* 1965; 6(5):472–6).

2.5.5 Silymarin

Silymarin is the extract from the seeds of the milk thistle plant *Silybum marianum* which is found in dry rocky soils of Southern and Western Europe and in some parts of the U.S. Silymarin extract is composed of three flavonoid molecules (silybin, silydianin, and silychristin). Silymarin is thought to have positive effects in the treatment of various forms of liver diseases and has been used for over 2,000 years. It is currently the most well researched plant extract in the treatment of liver disease (with over 450 published peer review papers).

Silymarin and one of its structural components, silibinin, have been well characterized as hepato-protective substances (Valenzuela A. et al. Biochemical bases of the pharmacological action of the flavonoid silymarin and of its structural isomer silibinin. *Biol Res.* 1994; 27(2):105–12). When ingested, silymarin undergoes enterohepatic recirculation and has higher concentrations in liver cells. Numerous studies have reported the hepatoprotective effects that silymarin has against a wide variety of toxins, including acetaminophen, ethanol, carbon tetra-chloride, and D-galactosamine, and against ischemic injury, radiation, iron toxicity, and viral hepatitis (McPartland J. M. Viral hepatitis treated with *Phyllanthus amarus* and milk thistle (*Silybum marianum*). *Complementary Medicine International* 1996; March/April: 40–42; Berkson B. M. A conservative triple antioxidant approach to the treatment of hepatitis C. Combination of alpha lipoic acid (thioctic acid), silymarin, and selenium: three case histories. *Med Klin.* 1999; 94 Suppl 3:84–9; Patrick L. Hepatitis C: epidemiology and review of complementary/alternative medicine treatments. *Altern Med Rev.* 1999; 4(4):220–38; Luper S. A review of plants used in the treatment of liver disease: Part 1. *Altern Med Rev.* 1998; 3:410–421; Gagliardi B. et al., Results of a double blind study on the effect of silymarin in the treatment of acute viral hepatitis, carried out at two medical centers. *Med Klin.* 1978; 73:1060–1065; Moscarelli S. et al., Therapeutic and antilipoperoxidant effects of silybin-phosphatidylcholine complex in chronic liver disease: preliminary results. *Curr Ther Res.* 1993; 53:98–102; Morazzoni P. et al., Comparative pharmacokinetics of silipide and silymarin in rats. *Eur J Drug Metab Pharmacokinet.* 1993; 18:289–297; Hruby K. et al. Chemotherapy of Amanita phalloides poisoning with intravenous silibinin. *Hum Toxicol.* 1983; 2:183–195; Sabeel A. I. et al. Intensive hemodialysis and hemoperfusion treatment of Amanita mushroom poisoning. *Mycopathologia* 1995; 131:107–114; Salmi H. A. et al. Effect of silymarin on chemical, functional, and morphological alterations of the liver; A double blind controlled study. *Scand J Gastroenterol.* 1982; 17:517–521; Buzzelli G. et al. A pilot study on the liver protective effect of silybin-phosphatidylcholine complex (1 dB 1016) in chronic active hepatitis. *Int J Clin Pharmacol Ther Toxicol.* 1993; 31:456–460; Feher I. et al. Liver-protective action of silymarin therapy in chronic alcoholic liver diseases. *Orv Hetil.* 1989; 130:2723–2727; Ferenci P. et al., Randomized controlled trial of silymarin treatment in patients with cirrhosis of the liver. *J Hepatol.* 1989; 9:105–113; Dehmlow C. et al. Inhibition of Kupffer cell functions as an explanation for the hepatoprotective properties of silibinin. *Hepatology* 1996; 23:749–754). Silymarin has also been shown to slow or reverse liver fibrosis in animals (Boigk G. et al. Silymarin retards collagen accumulation in early and advanced biliary fibrosis secondary to complete bile duct obliteration in rats. *Hepatology* 1997; 26:643–649).

2.5.6 Lipoic Acid

Lipoic acid, also known as and called interchangeably in this application alpha-lipoic acid, is a naturally occurring coenzyme found in most prokaryotic and eukaryotic microorganisms (Busby R. W. et al. Lipoic acid biosynthesis: LipA is an iron-sulfur protein. *J Am Chem Soc.* 1999; 121:4706–4707), as well as in many plant and animal tissues (Herbert A. A. et al. Lipoic acid content of *Escherichia coli* and other microorganisms. *Arch Microbiol.* 1975; 106:259–266).

Lipoic acid has therapeutic potential in conditions where oxidative stress is associated with liver damage (Bustamante J. et al., Alpha-lipoic acid in liver metabolism and disease. *Free Radic Biol Med.* 1998; 24(6):1023–39). Specifically, lipoic acid has been found to be useful in reducing serum aspartate transaminase and serum glutamyl transpeptidase, as well as improving liver histology (Marshall A. W. et al. Treatment of alcohol-related liver disease with thioctic acid: a six month randomized double-blind trial. Gut 1982; 23(12): 1088–93).

2.5.7 Vitamin E

Vitamin E is a fat-soluble vitamin that includes eight naturally occurring compounds in two classes designated as tocopherols and tocotrienols (Traber M. G. et al. Vitamin E: Beyond antioxidant function. *Am J Clin Nutr.* 1995; 62:1501S-9S). Alpha-tocopherol is the most active form of vitamin E in humans, and is a powerful biological antioxidant (Traber M. G. Vitamin E. In: Shils M E, Olson J A, Shike M, Ross AC, ed. Modern Nutrition in Health and Disease. 10th ed. Baltimore: Williams & Wilkins, 1999: 347–362; Farrell P. et al. Vitamin E. In: Shils M, Olson J A, and Shike M, ed. Modem Nutrition in Health and Disease. 8th ed. Philadelphia, Pa.: Lea and Febiger, 1994:326–341).

Vitamin E has been shown to protect against liver damage induced by oxidative stress in animal experiments by normalizing liver enzymes (Sun F. et al. Evaluation of oxidative stress based on lipid hydroperoxide, vitamin C and vitamin E during apoptosis and necrosis caused by thioacetamide in rat liver. *Biochim Biophys Acta.* 2000;1500(2):181–5; Nagita A. et al. Assessment of hepatic vitamin E status in adult patients with liver disease. *Hepatology* 1997; 26(2): 392–7; von Herbay A. et al. Vitamin E improves the aminotransferase status of patients suffering from viral hepatitis C: a randomized, double-blind, placebo-controlled study. *Free Radic Res.* 1997; 27(6):599–605). There is evidence that vitamin E can act as a supportive therapy to combat liver damage caused by oxidative stress in patients with continuously high levels of ALT even after anti-viral and anti-inflammatory drug therapy (Mahmood S. et al. Effect of vitamin E on serum aminotransferase and thioredoxin levels in patients with viral hepatitis C. *Free Radic Res.* 2003; 37(7):781–5).

2.5.8 Vitamin B-Complex

Vitamin B-complex generally refers to a selection of nutrients (e.g., thiamine (B1), riboflavin (B2), niacin (B3), pantothenic acid (B5), pyridoxine (B6), biotin (B7 or H), folic acid (B9), and cyanocobalamin (B12)) which have very similar properties and mostly work in synergy.

The therapeutic effects of B vitamins in treating chronic hepatitis have been investigated (Eberhardt G. et al. Controlled study of the therapeutic effect of B vitamins and an anabolic steroid in chronic hepatitis. *Dtsch Med Wochenschr.* 1975; 100(41):2074–82 (in German; Thaler H. Vitamin therapy in liver diseases. *Dtsch Med Wochenschr.* 1970; 95(30):1581–2 (in German)). In particular, numerous studies have shown that vitamin B12 is useful in treating hepatitis (Komar VI. Use of vitamin B12 in the combined therapy of viral hepatitis. Vopr Pitan. 1982; (1):26–9 (in Russian)). Cobalamins are stored in high concentrations in the human liver and thus are available to participate in the regulation of hepatotropic virus functions. Cyanocobalamin (vitamin B12), by inhibiting the HCV internal ribosome entry site (IRES)-dependent translation of a reporter gene in vitro in a dose-dependent manner without significantly affecting the cap-dependent mechanism, has a normalizing effect on the level of alanine aminotransferase of the blood (Takyar S. S. et al. Vitamin B12 stalls the 80 S ribosomal complex on the hepatitis C internal ribosome entry site. *J Mol Biol.* 2002 24; 319(1):1–8).

Citation of documents herein is not intended as an admission that any of the documents cited herein is pertinent prior art, or an admission that the cited documents are considered material to the patentability of the claims of the present application.

3. SUMMARY OF THE INVENTION

The present invention relates generally to antioxidants, compositions, and methods useful for reducing oxidative stress and/or lipid peroxidation, and/or treating or preventing chronic liver disease, chronic HCV infection, and/or NASH in a subject. In particular, the invention relates to compositions comprising one or more, or all of the antioxidants glycyrrhizin, *schisandra* extract, ascorbic acid, glutathione, silymarin, lipoic acid, d-alpha-tocopherol, and vitamin B-complex. More particular, the invention relates to compositions comprising one or more antioxidants listed herein for oral administration ("oral compositions") and compositions comprising one or more antioxidants listed herein to be administered parenterally ("parenteral compositions"), e.g., by infusion or intravenous injection. When administered to a subject, the compositions reduces oxidative stress, improve liver function tests, decrease viral load, improve liver histology, improve quality of life, and/or have no major side effects in the subject.

Methods of administering the antioxidants of the invention include, but are not limited to, oral, parenteral (e.g., subcutaneous, intramuscular, intraorbital, intracapsular, intraspinal, intrasternal, intravenous, intradermal, intraperitoneal, intraportal), epidural, and mucosal (e.g., intranasal) administration. In a specific embodiment, the antioxidants are parenterally administered to a subject. In another specific embodiment, the antioxidants are administered to a subject parenterally, by infusion. In another specific embodiment, the antioxidants are administered to a subject parenterally, by injection, preferably by intravenous injection.

In a preferred embodiment, one or more of the glycyrrhizin, *schisandra* extract, ascorbic acid, glutathione, silymarin, lipoic acid, d-alpha-tocopherol, and vitamin B-complex are administered orally to a patient, and one or more of the glycyrrhizin, *schisandra* extract, ascorbic acid, glutathione, silymarin, lipoic acid, d-alpha-tocopherol, and vitamin B-complex are administered parenterally to the patient. Parenteral administration includes, but is not limited to, subcutaneous administration, intramuscular administration, intraorbital administration, intracapsular administration, intraspinal administration, intrasternal administration, intravenous administration, intradermal administration, intraperitoneal administration, and intraportal administration.

In one embodiment, the invention relates to one or more antioxidants glycyrrhizin, *schisandra* extract, ascorbic acid, glutathione, silymarin, lipoic acid, and d-alpha-tocopherol.

In certain embodiments, the invention relates to oral compositions comprising one or more, or all of the antioxidants glycyrrhizin, *schisandra* extract, ascorbic acid, glutathione, silymarin, lipoic acid, and d-alpha-tocopherol. In one embodiment, the oral composition comprises one antioxidant selected from the group consisting of glycyrrhizin, *schisandra* extract, ascorbic acid, glutathione, silymarin, lipoic acid, and d-alpha-tocopherol. In another embodiment, the oral composition comprises glycyrrhizin, *schisandra* extract, ascorbic acid, glutathione, silymarin, lipoic acid, and d-alpha-tocopherol. In yet another embodiment, the oral composition comprises one or more, but not all of the antioxidants glycyrrhizin, *schisandra* extract, ascorbic acid, glutathione, silymarin, lipoic acid, and d-alpha-tocopherol.

In a specific embodiment, the oral composition comprises about 500 to 1,500 mg, preferably about 1,000 mg of glycyrrhizin. In a specific embodiment, the oral composition comprises about 1,000 to 3,000 mg, preferably about 1,500 mg of *schisandra* extract. In a specific embodiment, the oral composition comprises about 500 to 10,000 mg, preferably about 6,000 mg of ascorbic acid. In a specific embodiment, the oral composition comprises about 50 to 1,000 mg, preferably about 300 mg of glutathione. In a specific embodiment, the oral composition comprises about 80 to 1,000 mg, preferably about 750 mg of silymarin. In a specific embodiment, the oral composition comprises about 100 to 1,200 mg, preferably about 300 mg of lipoic acid. In a specific embodiment, the oral composition comprises about 200 to 1,600 iu, preferably about 800 iu of d-alpha-tocopherol.

In another specific embodiment, the oral composition comprises about 500 to 1,500 mg, preferably about 1,000 mg of glycyrrhizin; about 1,000 to 3,000 mg, preferably about 1,500 mg of *schisandra* extract; about 500 to 10,000 mg, preferably about 6,000 mg of ascorbic acid; about 50 to 1,000 mg, preferably about 300 mg of glutathione; about 80 to 1,000 mg, preferably about 750 mg of silymarin; about 100 to 1,200 mg, preferably about 300 mg of lipoic acid; and about 200 to 1,600 iu, preferably about 800 iu of d-alpha-tocopherol.

In preferred embodiments, the oral composition is in the form of a powder, solid, capsule, tablet, gel, solution, or emulsion.

In certain other embodiments, the invention relates to parenteral compositions comprising one or more, or all of the antioxidants glycyrrhizin, ascorbic acid, glutathione, and vitamin B-complex. In one embodiment, the parenteral composition comprises one antioxidant selected from the group consisting of glycyrrhizin, ascorbic acid, glutathione, and vitamin B-complex. In another embodiment, the parenteral composition comprises glycyrrhizin, ascorbic acid, glutathione, and vitamin B-complex. In yet another embodiment, the parenteral composition comprises one or more, but not all of the antioxidants glycyrrhizin, ascorbic acid, glutathione, and vitamin B-complex.

In a specific embodiment, the parenteral composition comprises about 10 to 500 mg, preferably about 120 mg of glycyrrhizin. In a specific embodiment, the parenteral composition comprises about 1,000 to 20,000 mg, preferably about 10,000 mg of ascorbic acid. In a specific embodiment, the parenteral composition comprises about 250 to 1,500 mg, preferably about 750 mg of glutathione. In a specific embodiment, the parenteral composition comprises about 0.1 to 100 ml, preferably about 1 ml of vitamin B-complex.

In another specific embodiment, the parenteral composition comprises about 10 to 500 mg, preferably about 120 mg of glycyrrhizin; about 1,000 to 20,000 mg, preferably about 10,000 mg of ascorbic acid; about 250 to 1,500 mg, preferably about 750 mg of glutathione; and about 0.1 to 100 ml, preferably about 1 ml of vitamin B-complex.

In preferred embodiments, the antioxidants in the parenteral composition are added, individually or as a mixture, to sterile water or normal saline for parenteral administration, preferably by infusion or intravenous injection.

In a specific embodiment, the compositions of the invention consist essentially of the antioxidants specified herein. Methods of making the antioxidants and compositions are further described infra. in Sections 5.1 and 5.2, respectively.

The present invention further provides a pharmaceutical pack or kit comprising one or more containers filled with one or more antioxidants and/or one or more oral compositions and/or parenteral compositions. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

The present invention also relates to methods of using the antioxidants and compositions.

In one embodiment, the antioxidants can be used alone or in combination with other oral compositions or parenteral compositions of the invention. In certain embodiments, the antioxidants can be used in combination with other therapies or therapeutic agents useful for reducing oxidative stress and/or lipid peroxide, and/or treating and/or preventing chronic liver disease, chronic HCV infection, and/or NASH. In a specific embodiment, the antioxidants of the invention can be used before, simultaneous, or after liver transplant. In another specific embodiment, the antioxidants can be used before, simultaneously, or after treatment with interferon and/or ribavirin.

In another embodiment, the oral compositions or parenteral compositions of the invention can be used alone or in combination with other oral compositions or parenteral compositions of the invention. In certain embodiments, the oral compositions and/or parenteral compositions can be used in combination with other therapies or therapeutic agents useful for reducing oxidative stress and/or lipid peroxide, and/or treating and/or preventing chronic liver disease, chronic HCV infection, and/or NASH. In a specific embodiment, the compositions of the invention can be used before, simultaneous, or after liver transplant. In another specific embodiment, the compositions of the invention can be used before, simultaneously, or after treatment with interferon and/or ribavirin.

The invention further relates to methods for reducing oxidative stress and lipid peroxidation, and methods for treating or preventing chronic liver disease, chronic HCV infection, and/or NASH in a subject. In a specific embodiment, the method comprises orally administering to a subject glycyrrhizin, *schisandra* extract, ascorbic acid, glutathione, silymarin, lipoic acid, and d-alpha-tocopherol, and parenterally administering to the subject glycyrrhizin, ascorbic acid, glutathione, and vitamin B-complex. In another specific embodiment, the method comprises orally administering to a subject glycyrrhizin, *schisandra* extract, ascorbic acid, glutathione, silymarin, lipoic acid, and d-alpha-tocopherol. In another specific embodiment, the method comprises parenterally administering to the subject glycyrrhizin, ascorbic acid, glutathione, and vitamin B-complex.

In a specific embodiment, the method comprises orally administering to a subject a first composition comprising glycyrrhizin, a second composition comprising *schisandra* extract, a third composition comprising ascorbic acid, a fourth composition comprising glutathione, a fifth composition comprising silymarin, a sixth composition comprising lipoic acid, and a seventh composition comprising d-alpha-tocopherol, and parenterally administering to the subject an eighth composition comprising glycyrrhizin, a ninth composition comprising ascorbic acid, a tenth composition comprising glutathione, and an eleventh composition comprising vitamin B-complex. In another specific embodiment, the method comprises orally administering to a subject a first composition comprising glycyrrhizin, a second composition comprising *schisandra* extract, a third composition comprising ascorbic acid, a fourth composition comprising glutathione, a fifth composition comprising silymarin, a sixth composition comprising lipoic acid, and a seventh composition comprising d-alpha-tocopherol. In another specific embodiment, the method comprises parenterally administering to the subject a first composition comprising glycyrrhizin, a second composition comprising ascorbic acid, a third composition comprising glutathione, and a fourth composition comprising vitamin B-complex.

In one embodiment, one or more antioxidants can be orally administered to a subject one to four times a day. In a specific embodiment, glycyrrhizin, *schisandra* extract, ascorbic acid, glutathione, silymarin, lipoic acid, and d-alpha-tocopherol are administered orally to a subject one to four times a day. In a specific embodiment, 1,000 mg of glycyrrhizin is administered orally to a subject once a day. In another specific embodiment, 1,500 mg of *schisandra* extract is administered orally to a subject once a day. In another specific embodiment, 6,000 mg of ascorbic acid is administered orally to a subject once a day. In another specific embodiment, 300 mg of glutathione is administered orally to a subject once a day. In another specific embodiment, 750 mg of silymarin is administered orally to a subject once a day. In another specific embodiment, 300 mg of lipoic acid administered orally to a subject once a day. In another specific embodiment, 800 iu of d-alpha-tocopherol is administered orally to a subject once a day. In yet another specific embodiment, 1,000 mg of glycyrrhizin, 1,500 mg of *schisandra* extract, 6,000 mg of ascorbic acid, 300 mg of glutathione, 750 mg of silymarin, 300 mg of lipoic acid, and 800 iu of d-alpha-tocopherol are administered orally to a subject once a day.

The antioxidants can be directly ingested by the subject or used as an additive to be incorporated into food to be consumed by the subject. Dietary supplements comprising the antioxidants are also encompassed by the invention.

In one embodiment, one or more oral compositions can be orally administered to a subject one to four times a day. In a specific embodiment, an oral composition comprising glycyrrhizin, *schisandra* extract, ascorbic acid, glutathione, silymarin, lipoic acid, and d-alpha-tocopherol is administered orally to a subject one to four times a day. In a preferred embodiment, a first oral composition comprising 1,000 mg of glycyrrhizin, a second oral composition comprising 1,500 mg of *schisandra* extract, a third oral composition comprising 6,000 mg of ascorbic acid, a fourth oral composition comprising 300 mg of glutathione, a fifth oral composition comprising 750 mg of silymarin, a sixth oral composition comprising 300 mg of lipoic acid, and a seventh oral composition comprising 800 iu of d-alpha-toco pherol is administered orally to a subject once a day. In another preferred embodiment, an oral composition comprising 1,000 mg of glycyrrhizin, 1,500 mg of *schisandra* extract, 6,000 mg of ascorbic acid, 300 mg of glutathione, 750 mg of silymarin, 300 mg of lipoic acid, and 800 iu of d-alpha-tocopherol is administered orally to a subject once a day.

In another specific embodiment, a first oral composition comprising glycyrrhizin, a second oral composition comprising *schisandra* extract, a third oral composition comprising ascorbic acid, a fourth oral composition comprising glutathione, a fifth oral composition comprising silymarin, a sixth oral composition comprising lipoic acid, and a seventh oral composition comprising d-alpha-tocopherol are administered orally to a subject one to four times a day. In a preferred embodiment, a first oral composition comprising glycyrrhizin is administered orally to a subject in two units of 250 mg, two times a day. In another preferred embodiment, a second oral composition comprising *schisandra* extract is administered orally to a subject in one unit of 500 mg, three times a day. In another preferred embodiment, a third oral composition comprising ascorbic acid is administered orally to a subject in four units of 500 mg, three times a day. In another preferred embodiment, a fourth oral composition comprising glutathione is administered orally to a subject in one unit of 150 mg, two times a day. In another preferred embodiment, a fifth oral composition comprising silymarin is administered orally to a subject in one unit of 250 mg, three times a day. In another preferred embodiment, a sixth oral composition comprising lipoic acid is administered orally to a subject in one unit of 150 mg, two times a day. In another preferred embodiment, a seventh oral composition comprising d-alpha-tocopherol is administered orally to a subject in two units of 400 iu, once a day. The units can be in the form of a powder, solid, capsule, tablet, gel, solution, or emulsion.

The oral compositions can be directly ingested by the subject or used as an additive to be incorporated into food to be consumed by the subject. Dietary supplements comprising the oral compositions are also encompassed by the invention.

In another embodiment, one or more antioxidants can be administered to a subject one to four times a week. In a specific embodiment, glycyrrhizin, ascorbic acid, glutathione, and vitamin B-complex are administered to a subject one to four times a week. In a specific embodiment, 240 mg of glycyrrhizin is administered to a subject once a week. In another specific embodiment, 20,000 mg of ascorbic acid is administered to a subject once a week. In another specific embodiment, 1,500 mg of glutathione is administered to a subject once a week. In another specific embodiment, 2.0 ml of vitamin B-complex is administered to a subject once a week. In yet another specific embodiment, 240 mg of glycyrrhizin, 20,000 mg of ascorbic acid, 1,500 mg of glutathione, and 2.0 ml of vitamin B-complex are administered to a subject once a week.

In another embodiment, a parenteral composition is administered to a subject one to four times a week. In a specific embodiment, a parenteral composition comprising glycyrrhizin, ascorbic acid, glutathione, and vitamin B-complex is administered to a subject one to four times a week. In a preferred embodiment, a parenteral composition comprising 240 mg of glycyrrhizin, 20,000 mg of ascorbic acid, 1,500 mg of glutathione, and 2.0 ml of vitamin B-complex is administered to a subject once a week.

In another specific embodiment, a first parenteral composition comprising glycyrrhizin, a second parenteral composition comprising ascorbic acid, a third parenteral composition comprising glutathione, and a fourth parenteral composition comprising vitamin B-complex are administered to a subject one to four times a week. In a preferred embodiment, a first parenteral composition comprising 120 mg of glycyrrhizin is administered to a subject twice a week. In another preferred embodiment, a second parenteral composition comprising 10,000 mg of ascorbic acid is administered to a subject twice a week. In another preferred embodiment, a third parenteral composition comprising 750 mg of glutathione is administered to a subject twice a week. In yet another preferred embodiment, a fourth parenteral composition comprising 1 ml of B-complex is administered to a subject twice a week. In a preferred embodiment, a first parenteral composition comprising 120 mg of glycyrrhizin, a second parenteral composition comprising 10,000 mg of ascorbic acid, a third parenteral composition comprising 750 mg of glutathione, and a fourth parenteral composition comprising 1 ml of B-complex is administered together to a subject twice a week.

Methods of administering the parenteral compositions of the invention include, but are not limited to, parenteral (e.g., subcutaneous, intramuscular, intraorbital, intracapsular, intraspinal, intrasternal, intravenous, intradermal, intraperitoneal, intraportal), epidural, and mucosal (e.g., intranasal) administration. In a specific embodiment, the parenteral compositions are parenterally administered to a subject. In another specific embodiment, the parenteral compositions are administered to a subject parenterally, by infusion. In another specific embodiment, the parenteral compositions are administered to a subject parenterally, by injection, preferably by intravenous injection.

The subject is preferably a mammal such as a non-primate (e.g., a cow, pig, horse, cat, dog, rat, mouse, etc.) and a primate (e.g., a monkey, chimpanzee, human, etc.), most preferably a human. In certain other embodiments, the subject is partially responsive or not responsive to treatment with interferon and/or ribavirin.

In various embodiments, the antioxidants, oral compositions and/or parenteral compositions of the invention are used to reduce oxidative stress or lipid peroxidation, or to treat or prevent chronic liver disease, chronic HCV infection, and/or NASH in a subject. In a specific embodiment, one or more antioxidants, oral compositions and/or parenteral compositions can be used to reduce the level of reactive oxygen species in a biological sample (e.g., tissue, blood, serum, cells, plasma) from a subject which received the one or more antioxidants, oral compositions and/or parenteral compositions. In a specific embodiment, one or more antioxidants, oral compositions and/or parenteral compositions can be used to increase the level of antioxidants in a biological sample (e.g., tissue, blood, serum, cells, plasma) from a subject which received the one or more antioxidants, oral compositions and/or parenteral compositions. In a specific embodiment, one or more antioxidants, oral compositions and/or parenteral compositions can be used to reduce the level of adducts formed in a subject which received the one or more antioxidants, oral compositions and/or parenteral compositions. In a specific embodiment, one or more antioxidants, oral compositions and/or parenteral compositions can be used to reduce liver enzymes in a subject which received the one or more antioxidants, oral compositions and/or parenteral compositions. In another specific embodiment, one or more antioxidants, oral compositions and/or parenteral compositions can be used to reduce viral load in a subject which received the one or more antioxidants, oral compositions and/or parenteral compositions. In another specific embodiment, the antioxidants, oral compositions and/or parenteral compositions can be used to improve liver histology (e.g., cirrhosis, fibrosis, lobular hepatitis or periportal bridging necrosis) in a subject which received the antioxidants, oral compositions and/or parenteral compositions. In yet another specific embodiment, the antioxidants, oral compositions and/or parenteral compositions can be used to improve quality of life (e.g., general health, physical health, emotional health) in a subject which received the antioxidants, oral compositions and/or parenteral compositions.

4. BRIEF DESCRIPTION OF THE FIGURES

FIG. 1 shows the schedule of an open labeled, non-randomized, one center clinical trial as described in Section 6, infra.

FIG. 2 shows the Histological Activity Index (HAI) scoring system used in the clinical trial.

Figure 3:
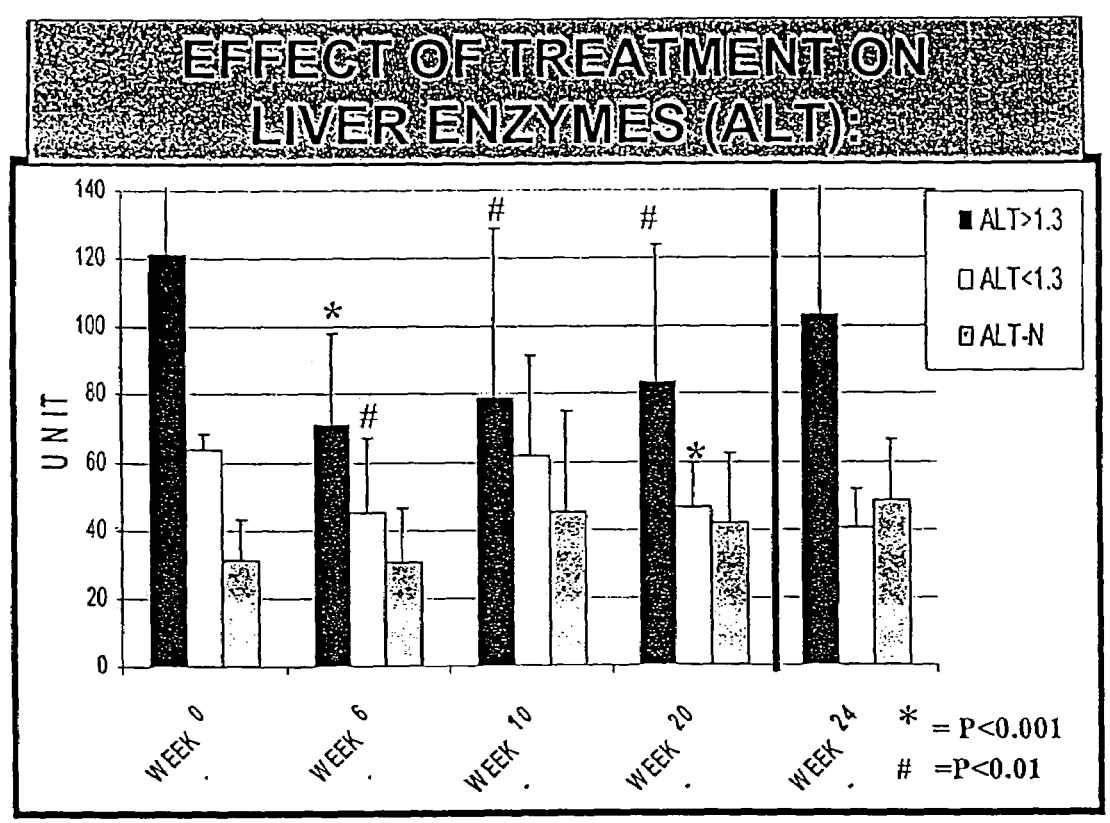

FIG. 3 shows the change in liver enzyme ALT of the subjects at week 0 (before treatment), week 6, week 10 (after iv treatment), week 20 (after oral treatment), and week 24 (post-treatment).

Figure 4:
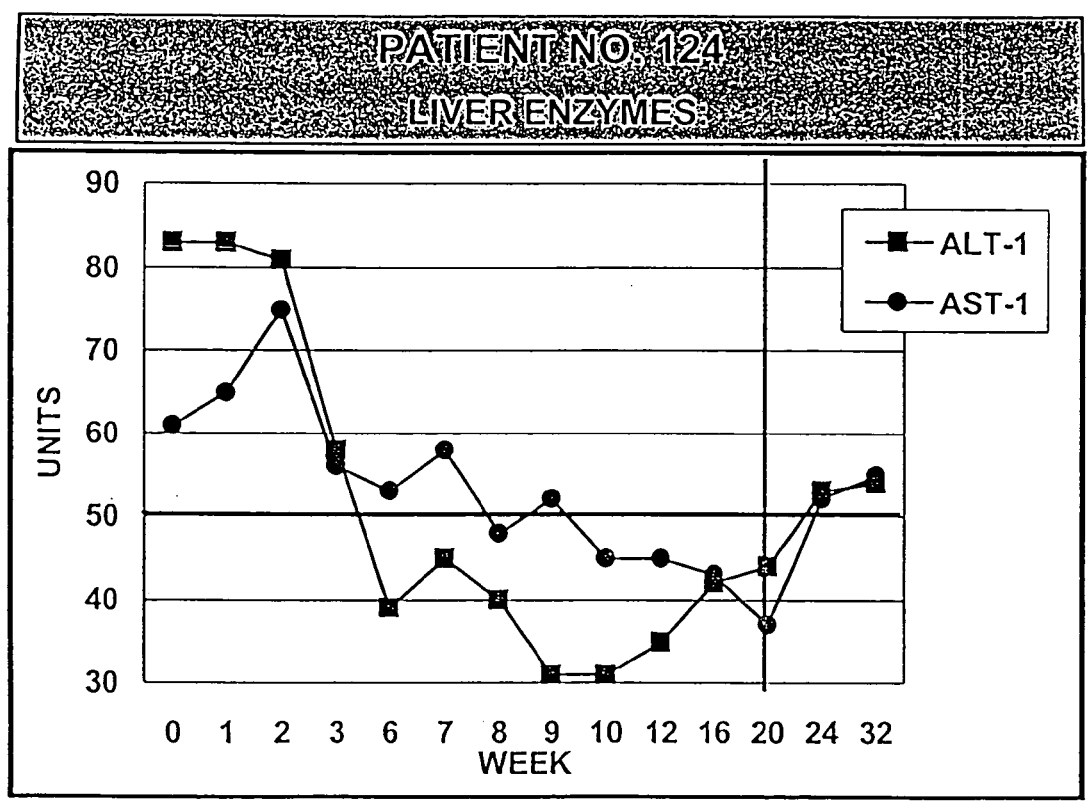

FIG. 4 shows the changes in liver enzymes ALT and AST of patient no. 124.

Figure 5:
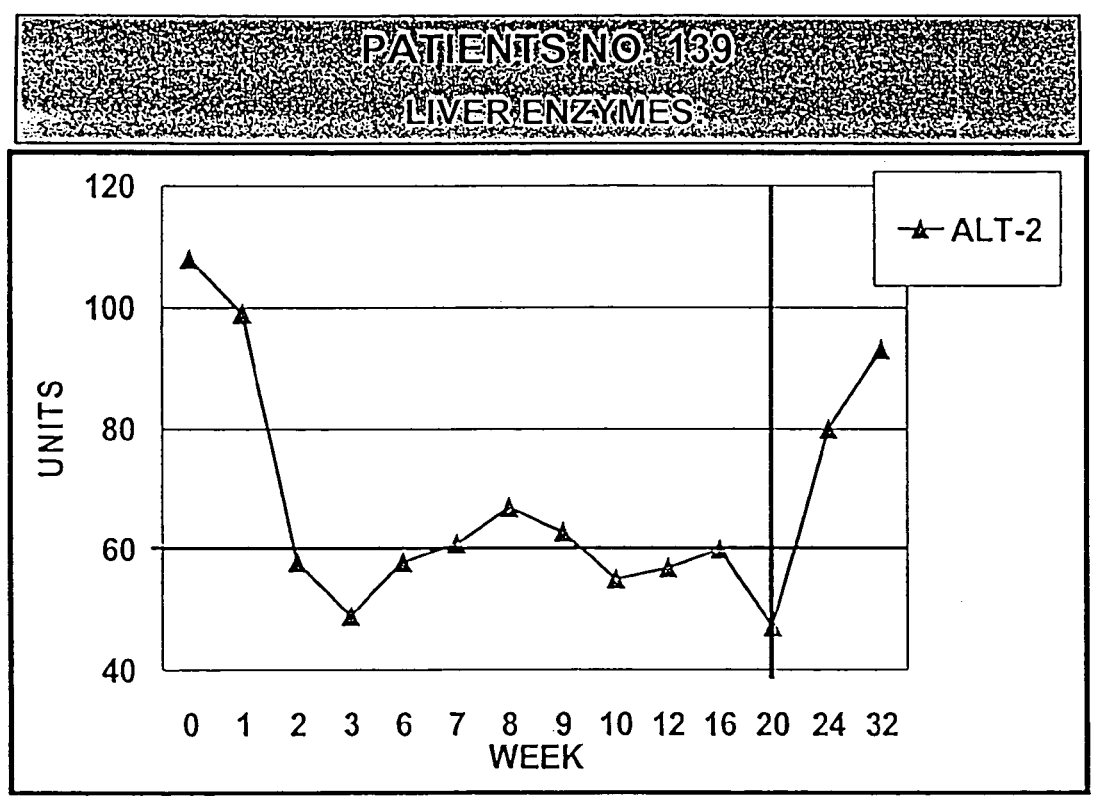

FIG. 5 shows the changes in liver enzyme ALT of patient no. 139.

Figure 6:
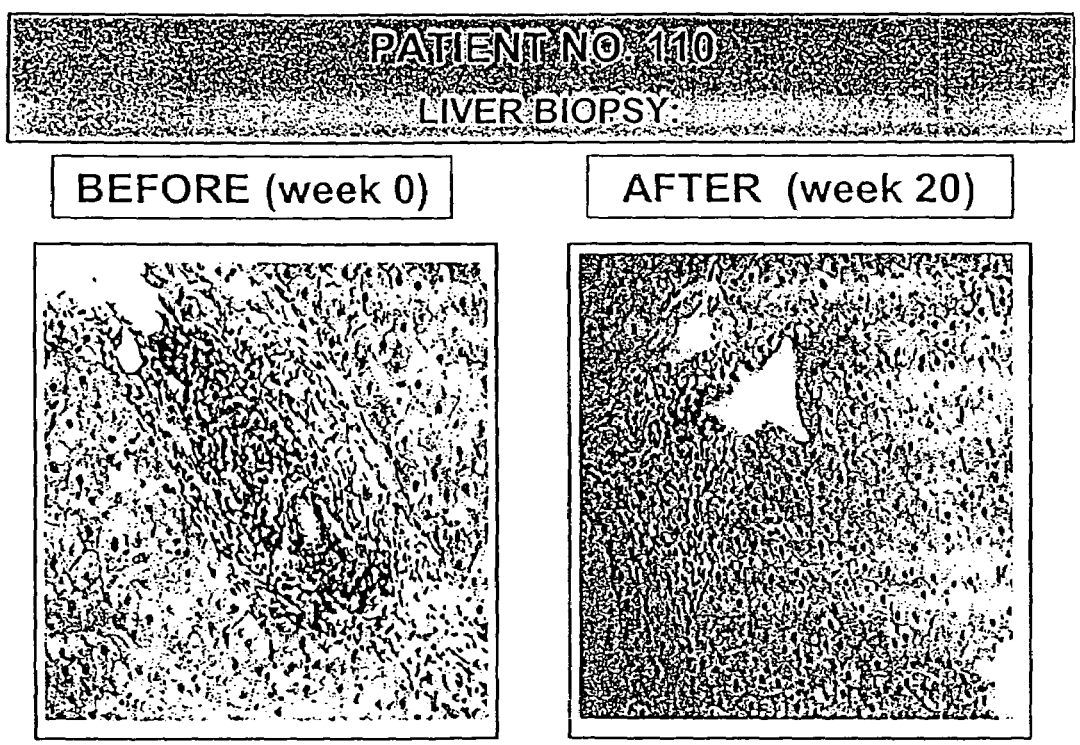

FIG. 6 shows the changes in liver biopsy of patient no. 110 before treatment (week 0) and after treatment (week 20).

Figure 7:
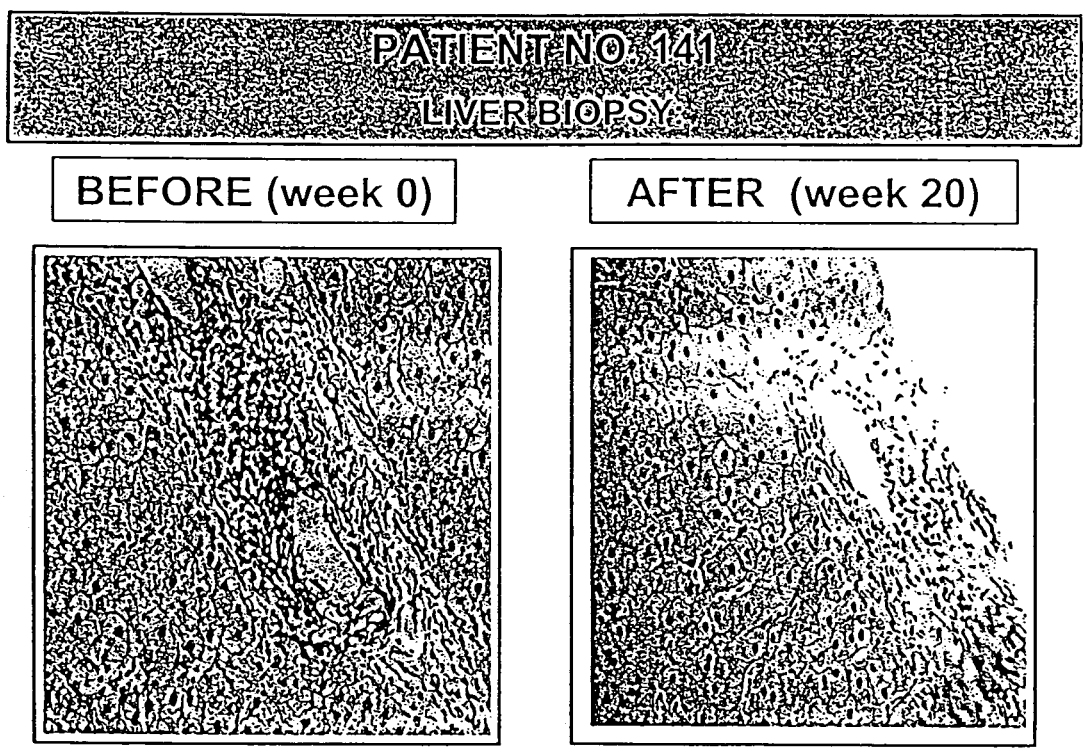

FIG. 7 shows the changes in liver biopsy of patient no. 141 before treatment (week 0) and after treatment (week 20).

Figure 8:
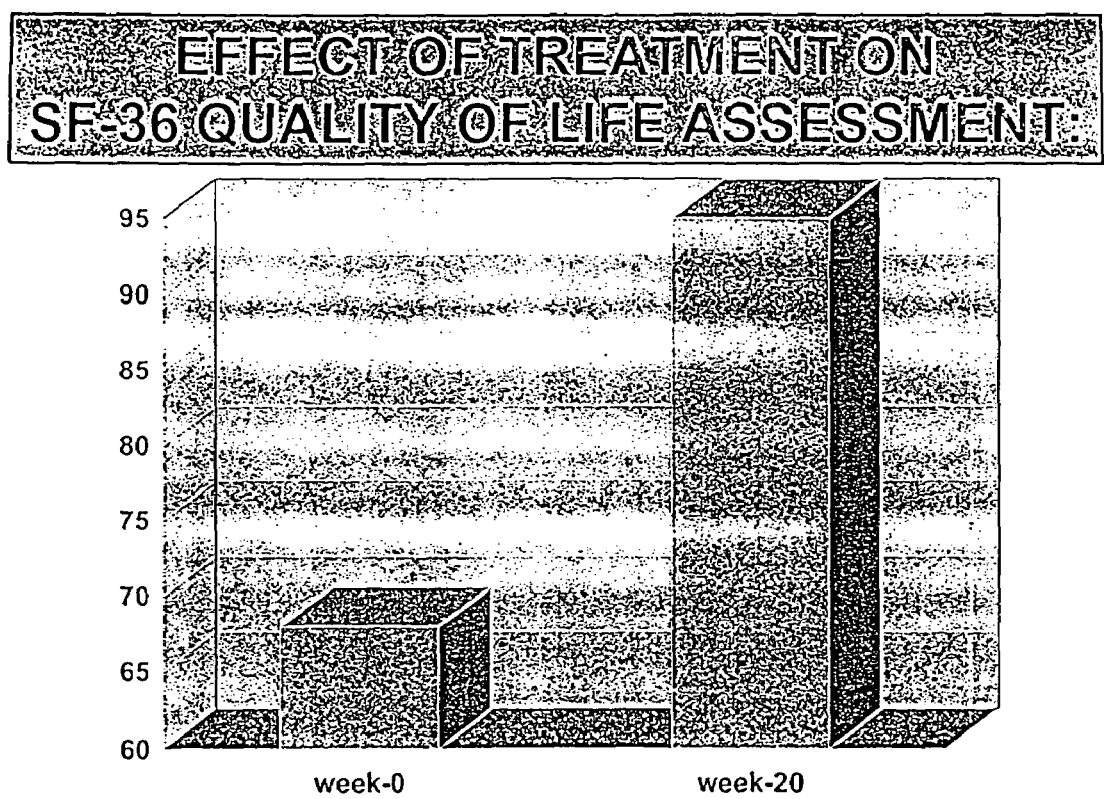

FIG. 8 shows the changes in quality of life of the subjects before treatment (week 0) and after treatment (week 20).

5. DETAILED DESCRIPTION OF THE INVENTION

The present invention relates to compositions comprising one or more, or all of the antioxidants glycyrrhizin, *schisandra* extract, ascorbic acid, glutathione, silymarin, lipoic acid, d-alpha-tocopherol, and vitamin B-complex. In particular, the invention relates to compositions for oral administration ("oral compositions") and compositions to be administered parenterally ("parenteral compositions"), e.g., by infusion or intravenous injection. In one embodiment, an oral composition comprises an antioxidant selected from the group consisting of glycyrrhizin, *schisandra* extract, ascorbic acid, glutathione, silymarin, lipoic acid, and d-alpha-tocopherol. In another embodiment, an oral composition comprises glycyrrhizin, *schisandra* extract, ascorbic acid, glutathione, silymarin, lipoic acid, and d-alpha-tocopherol. In another embodiment, an oral composition comprises one or more, but not all of glycyrrhizin, *schisandra* extract, ascorbic acid, glutathione, silymarin, lipoic acid, and d-alpha-tocopherol. In yet another embodiment, a parenteral composition comprises an antioxidant selected from the group consisting of glycyrrhizin, ascorbic acid, glutathione, and vitamin B-complex. In yet another embodiment, a parenteral composition comprises glycyrrhizin, ascorbic acid, glutathione, and vitamin B-complex. In yet another embodiment, a parenteral composition comprises one or more, but not all of glycyrrhizin, ascorbic acid, glutathione, and vitamin B-complex.

The antioxidants, oral compositions and parenteral compositions of the invention are useful for reducing oxidative stress and/or lipid peroxidation, and/or for treating or preventing chronic liver disease, chronic HCV infection, and/or NASH. In a specific embodiment, the method comprises orally administering to a subject one or more antioxidants glycyrrhizin, *schisandra* extract, ascorbic acid, glutathione, silymarin, lipoic acid, and d-alpha-tocopherol, and parenterally administering to the subject glycyrrhizin, ascorbic acid, glutathione, and vitamin B-complex. In another specific embodiment, the method comprises orally administering to a subject glycyrrhizin, *schisandra* extract, ascorbic acid, glutathione, silymarin, lipoic acid, and d-alpha-tocopherol. In another specific embodiment, the method comprises parenterally administering to a subject glycyrrhizin, ascorbic acid, glutathione, and vitamin B-complex. In yet another specific embodiment, the method comprises orally administering to a subject a first composition comprising glycyrrhizin, a second composition comprising *schisandra* extract, a third composition comprising ascorbic acid, a fourth composition comprising glutathione, a fifth composition comprising silymarin, a sixth composition comprising lipoic acid, and a seventh composition comprising d-alpha-tocopherol, and parenterally administering to the subject an eighth composition comprising glycyrrhizin, a ninth composition comprising ascorbic acid, a tenth composition comprising glutathione, and an eleventh composition comprising vitamin B-complex. In yet another specific embodiment, the method comprises orally administering to a subject a first composition comprising glycyrrhizin, a second composition comprising *schisandra* extract, a third composition comprising ascorbic acid, a fourth composition comprising glutathione, a fifth composition comprising silymarin, a sixth composition comprising lipoic acid, and a seventh composition comprising d-alpha-tocopherol. In yet another specific embodiment, the method comprises parenterally administering to a subject a first composition comprising glycyrrhizin, a second composition comprising ascorbic acid, a third composition comprising glutathione, and a fourth composition comprising vitamin B-complex.

Described below in Section 5.1 are non-limiting examples of different kinds of antioxidants that can be used in the compositions and methods of the invention and methods for preparing the antioxidants. Section 5.2 describes methods of making the oral compositions and parenteral compositions of the invention. Section 5.3 describes methods of using the antioxidants, oral compositions and/or parenteral compositions to reduce oxidative stress and/or lipid peroxidation in a subject, and methods of using the antioxidants, oral compositions and/or parenteral compositions to treat and/or prevent chronic liver disease, chronic HCV infection, and/or NASH in a subject. The examples in Sections 6 to 11 demonstrate the therapeutic benefits of the antioxidants and compositions of the invention. In certain embodiments, the antioxidants and compositions are characterized by their ability to (i) reduce oxidative stress in a subject with chronic liver disease, chronic HCV infection and/or NASH; (ii) reduce liver enzymes in a subject with chronic liver disease, chronic HCV infection and/or NASH; (iii) reduce viral load in a subject with chronic liver disease, chronic HCV infection and/or NASH; (iv) improve liver histology of a subject with chronic liver disease, chronic HCV infection and/or NASH; and/or (v) improve quality of life of a subject with chronic liver disease, chronic HCV infection and/or NASH.

5.1 Antioxidants 5.1.1 Glycyrrhizin

Glycyrrhizin for use in the compositions and methods of the present invention can be extracted from the root of the licorice plant (*Glycyrriza glabra, Glycyrriza uralensis*), which is native to Turkey, Iraq, Spain, Greece, and northern China and is extensively cultivated in Russia, Spain, Persia, and India, by methods well known to those skilled in the art (see, e.g., Felter, H. W. et al. Dietary Supplement Verification Program (DSVP) of the United States Pharmacopeia and the National Formulary (USP-NF). King's American Dispensatory, 1898; Huang W. A. et al. [An orthogonal method for comparing extracting techniques of licorice root extract] (in Chinese). *Zhongguo Zhong Yao Za Zhi.* 1994; 19(5):283–4, 319; Nishizawa H. et al. [Practical Optimization Method for Dual-Flow Countercurrent Extraction: Purification of Glycyrrhizin] (in Japanese). *The Japan Society for Analytical Chemistry* 1992; 8(3):367–374; Zheng L. et al. [Separation and quantitative determination of three saponins in licorice root by high performance liquid chromatography] (in Chinese). *Yao Xue Xue Bao.* 1991; 26(1): 53–8; Ha Y. et al. Chiral separation of glycyrrhetinic acid by high-performance liquid chromatography. *J Pharm Biomed Anal.* 1991; 9(10–12):805–9, each of which is incorporated by reference herein in its entirety). In a specific embodiment, the glycyrrhizin used in the compositions of the present invention can be extracted from licorice root by high-performance liquid chromatography using a methanol-water (65:35, v/v) mobile phase. In certain embodiments, at least 5%, 6%, 7%, 8%, 9%, 10%, 12%, 13%, 14%, 15%, 16%, 17%, 18%, 19%, 20%, 21%, 22%, 23%, 24%, 25%, 30%, or more of licorice root extract is glycyrrhizin. In a specific embodiment, at least 16% of licorice root extract is glycyrrhizin.

Alternatively, glycyrrhizin for use in the compositions and methods of the present invention can also be prepared from crude licorice root. In one embodiment, the licorice root can be processed, washed, dried, dehydrated, crushed, ground and/or frozen prior to isolating the glycyrrhizin. Licorice root can also be boiled in water to make a glycyrrhizin solution. In a specific embodiment, about 5 g of licorice root can be boiled in about 500 ml of water for 15 min to make a glycyrrhizin solution.

Glycyrrhizin, also known as glycyrrhizinic acid, glycyrrhetic acid, glycyrrhetinic acid glycoside, and (3-beta,20-beta)-20-carboxy-11-oxo-30-norolean-12-en-3-yl 2-O-beta-D-glucopyranuronosyl-alpha-D-glucopyranosiduronic acid, can also be synthesized by methods well known to those skilled in the art (see, e.g., Morishima N. et al. Synthesis of glycyrrhizin analogues containing fluorinated beta(1->2)-linked disaccharides. *Bioorg Med Chem.* 1996; 4(11):1799–808; Brieskorn C. H. et al. [Synthesis of glycyrrhizin acid and glycyrrhetin acid derivatives] (in German). *Arch Pharm Ber Dtsch Pharm Ges.* 1970; 303(11):905–12; Kanaoka M. et al. Synthesis and separation of 18 beta-glycyrrhetyl monoglucuronide from serum of a patient with glycyrrhizin-induced pseudo-aldosteronism. *Chem Pharm Bull.* (Tokyo) 1986; 34(12):4978–83, each of which is incorporated by reference herein in its entirety). In a specific embodiment, the glycyrrhizin used in the compositions of the present invention has a molecular formula of $C_{42}H_{62}O_{16}$, and a molecular weight of 822.94 g per mole.

In another embodiment, the glycyrrhizin used in the compositions and methods of the present invention is purchased. Glycyrrhizin is commercially available in the form of a powder, solid, capsule, tablet, gel, solution, or emulsion. For example, glycyrrhizin can be purchased from companies such as Sigma Chemical Company (St. Louis, Mo., USA) or health and herb stores such as General Nutrition Centers, Inc. (Pittsburgh, Pa., USA). In a specific embodiment, the glycyrrhizin used in the compositions and methods of the present invention can be purchased from Vital Nutrients (Middletown, Conn., USA). In a more specific embodiment, the glycyrrhizin can be purchased from Vital Nutrients in 250 mg capsule units.

5.1.2 *schisandra* Extract (Wu Wei Zi)

*Schisandra* extract for use in the compositions and methods of the present invention can be extracted from the berries of *schisandra* (*Schisandra chinensis*) by methods well known to those skilled in the art (see, e.g., Yang S. B. et al. [Study on supercritical CO2 fluid extraction and separation of components from fruits of *Schisandra sphenanthera*] (in Chinese). *Zhongguo Zhong Yao Za Zhi.* 2001; 26(11):755–7; Wang K. et al. [Determination of the active ingredients in Chinese drug wuweizi (*Schisandra chinensis*) by TLC-densitometry] (in Chinese). *Yao Xue Xue Bao.* 1990; 25(1): 49–53, each of which is incorporated by reference herein in its entirety). In a specific embodiment, the *schisandra* extract can be extracted from the berries of *schisandra* using hexane. In certain embodiments, *schisandra* extract is concentrated to a ratio of 50:1, 40:1, 30:1, 20:1, 15:1, 10:1, 5:1, 4:1, 3:1, or 2:1 relative to the starting extract. In a preferred embodiment, the *schisandra* extract used in the compositions of the present invention is concentrated to 30:1.

Alternatively, *schisandra* extract for use in the compositions and methods of the present invention can also be prepared from crude *schisandra* berries. In one embodiment, the berries of *schisandra* can be processed, washed, dried, dehydrated, crushed, ground and/or frozen prior to isolating the *schisandra* extract. *Schisandra* berries can also be boiled in water to make a *schisandra* solution. In a specific embodiment, about 5 g of *schisandra* berries can be boiled in about 500 ml of water for 15 min to make a *schisandra* solution.

In one embodiment, the *schisandra* extract used in the compositions and methods of the present invention is extracted from the seeds of the *schisandra* fruit which contain the active ingredient lignan. The *schisandra* extract can be standardized to, e.g., 20 mg lignan content (equivalent to 1.5 g crude *schisandra*). In certain embodiments, the *schisandra* extract used in the compositions of the invention is 50:1, 40:1, 30:1, 25:1, 20:1, 15:1, 10:1, 9:1, 8:1, 7:1, 6:1, 5:1, 4:1, 3:1, 2:1, or 1:1 concentrated relative to the starting extract. In a specific embodiment, the *schisandra* extract is 30:1.

*Schisandra* extract, which comprises active lignans constituents (e.g., schisandrols A and B, schisandrin A/B/C, schisantherin A–E, gomisin A, angeloylgomisin, anwulignan, wulignan, epiwulignan, epischisandron, deoxyschizandrin, gomisins, and pregomisin), can also be synthesized by methods well known to those skilled in the art (see, e.g., Chang J. et al. Total synthesis of schizandrin, the main active ingredient isolated from the Chinese herbal medicine fructus *schisandra* [in Chinese]. Yao Xue Xue Bao. 1998; 33(6): 424–8; Lee W. et al. Application of countercurrent chromatography/thermospray mass spectrometry for the identification of bioactive lignans from plant natural products. *Anal Chem.* 1990; 62(3):244–8; Han S. K. et al. Solubilization of biphenyl dimethyl dicarboxylate by cosolvency. *Drug Dev Ind Pharm.* 1999; 25(11):1193–7; Li X. Y. Bioactivity of neolignans from fructus *schisandra*. *Mem Inst Oswaldo Cruz.* 1991; 86 Suppl 2:31–7; Chen Y. et al. [Lignans from *schisandra propinqua* (Wall.) Hook. f. et Thoms] (in Chinese). *Zhong Yao Cai.* 2001; 24(2):105–7; Li R. T. et al. Micrandilactone A: a novel triterpene from *Schisandra micrantha*. *Org Lett.* 2003; 5(7):1023–6; Song W. [Quality of *Schisandra incarnata* Stapf] (in Chinese). *Zhongguo Zhong Yao Za Zhi.* 1991; 16(4):204–6, 253, each of which is incorporated by reference herein in its entirety). In a specific embodiment, the *schisandra* extract consists essentially of purified lignans that can, for example, be extracted and separated from the berries of *schisandra* by supercritical carbon dioxide fluid extraction technology.

In another embodiment, the *schisandra* extract used in the compositions and methods of the present invention is purchased. *Schisandra* extract is commercially available in the form of a powder, solid, capsule, tablet, gel, solution, or emulsion. For example, *schisandra* extract can be purchased from companies such as Sino-American Joint Venture Panjin Green Biological Development Co., Ltd. (Panjin City, Liaoning, China) or health and herb stores such as Castletown Health Store, Inc. (Castletown, Isle of Man, British Isles). In a specific embodiment, the *schisandra* extract used in the compositions and methods of the present invention can be purchased from Vital Nutrients (Middletown, Conn., USA). In a more specific embodiment, the *schisandra* extract can be purchased from Vital Nutrients in 500 mg capsule units.

5.1.3 Ascorbic Acid (Vitamin C)

Ascorbic acid for use in the compositions and methods of the present invention can be prepared from fruit sources such as citrus fruits, fresh strawberries, cantaloupe, pineapples and guava; and vegetable sources such as broccoli, Brussels sprouts, tomatoes, spinach, kale, green peppers, cabbage and turnips. In one embodiment, the fruit or vegetable source can be processed, washed, dried, dehydrated, crushed, ground and/or frozen prior to isolating the ascorbic acid. In a specific embodiment, the fruit or vegetable source can be dehydrated and ground into fine powder.

In a specific embodiment, the ascorbic acid used in the compositions and methods of the present invention is buffered ascorbic acid. In a more specific embodiment, the buffered ascorbic acid comprises calcium ascorbate, magnesium ascorbate, and potassium ascorbate to create a neutral pH vitamin C. Buffered ascorbic acid can lessen possible gastric irritation in sensitive individuals.

In certain other embodiments, the ascorbic acid used in the compositions and methods of the invention can be synthesized and purified by methods well known to those skilled in the art (see, e.g., Chatterjee I. B. et al. Synthesis and some major functions of vitamin C in animals. *Ann N Y Acad Sci.* 1975; 258:24–47; Kasai T. et al. Synthesis and antiscorbutic activity of vitamin C analogue: L-threo-hex-2-enaro-1,4-lactone ethyl ester in the guinea pig. *Int J Vitam Nutr Res.* 1993; 63(3):208–11; Morisaki K. et al. Synthesis of novel vitamin C phosphodiesters: stability and antioxidant activity. *Carbohydr Res.* 1996; 286:123–38; Kyle R. A. et al. Walter Haworth—synthesis of vitamin C. *Mayo Clin Proc.* 2002; 77(2):108; Rajalackshmi R. et al. Vitamin C synthesis in rats fed on diets deficient or normal in iron content. *Br J Nutr.* 1967; 21(2):333–40, each of which is incorporated by reference herein in its entirety). In a specific embodiment, the ascorbic acid used in the compositions of the present invention has a molecular formula of $C_6H_8O_6$, and a molecular weight of 176.1 g per mole.

In another embodiment, the ascorbic acid used in the compositions and methods of the present invention is purchased. Ascorbic acid is commercially available in the form of a powder, solid, capsule, tablet, gel, solution, or emulsion. For example, ascorbic acid can be purchased from companies such as such as Sigma Chemical Company (St. Louis, Mo., USA) or health and herb stores such as General Nutrition Centers, Inc. (Pittsburgh, Pa., USA). In a specific embodiment, the ascorbic acid used in the compositions and methods of the present invention can be purchased from Vital Nutrients (Middletown, Conn., USA). In a more specific embodiment, the ascorbic acid can be purchased from Vital Nutrients in 500 mg capsule units.

5.1.4 Glutathione

Glutathione exists in two forms: the antioxidant "reduced glutathione" and the oxidized form. As used herein, the term "glutathione" refers to reduced glutathione. In a specific embodiment, the compositions of the present invention comprises glutathione. In a more specific embodiment, the glutathione used in the compositions and methods of the present invention is L-glutathione (reduced).

The glutathione for use in the compositions and methods of the present invention can be prepared from food sources such as avocado, watermelon, asparagus, grapefruit, potato, acorn squash, strawberries, orange, tomato, cantaloupe, broccoli, okra, peach, zucchini, and spinach. In one embodiment, the food source can be processed, washed, dried, dehydrated, crushed, ground and/or frozen prior to isolating the glutathione.

Alternatively, glutathione, which is a tri-peptide of three amino acids: glycine, glutamine (glutamic acid), and cysteine, can also be synthesized by methods well known to those skilled in the art (see, e.g., Bea F. et al. Induction of glutathione synthesis in macrophages by oxidized low-density lipoproteins is mediated by consensus antioxidant response elements. *Circ Res.* 2003; 92(4):386–93; Okumura R. et al. Synthesis of hydroxymethylglutathione from glutathione and L-serine catalyzed by carboxypeptidase Y. *Biosci Biotechnol Biochem.* 2003; 67(2):434–7; Cacciatore I. Synthesis and biological evaluation of the disulfide form of the glutathione analogue gamma-(L-glutamyl)-L-cysteinyl-L-aspartyl-L-cysteine. *Bioorg Chem.* 2003; 31(2):107–19; Dickinson D. A. et al. Cytoprotection against oxidative stress and the regulation of glutathione synthesis. *Biol. Chem.* 2003; 384(4):527–37; Scharf G. et al. Enhancement of glutathione and g-glutamylcysteine synthetase, the rate limiting enzyme of glutathione synthesis, by chemoprotective plant-derived food and beverage components in the human hepatoma cell line HepG2. *Nutr Cancer.* 2003; 45(1):74–83; Meister A. et al. Glutathione. *Annu Rev Biochem.* 1983; 52:711–60, each of which is incorporated by reference herein in its entirety). In a specific embodiment, reduced glutathione has a molecular formula of $C_{10}H_{17}N_3O_6S$, and a molecular weight of 307.3 g per mole. In a more specific embodiment, the L-glutathione used in the compositions of the present invention is synthesized from the three amino acids L-glutamic acid, L-cysteine, and glycine.

In another embodiment, the glutathione used in the compositions and methods of the present invention is purchased. Glutathione is commercially available in the form of a powder, solid, capsule, tablet, gel, solution, or emulsion. For example, glutathione can be purchased from companies such as Sigma Chemical Company (St. Louis, Mo., USA) or health and herb stores such as General Nutrition Centers, Inc. (Pittsburgh, Pa., USA). In a specific embodiment, the glutathione used in the compositions and methods of the present invention can be purchased from Vital Nutrients (Middletown, Conn., USA). In a more specific embodiment, the glutathione can be purchased from Vital Nutrients in 100 mg capsule units.

5.1.5 Silymarin

Silymarin for use in the compositions and methods of the present invention can be extracted from the seeds of the milk thistle plant (*Silybum marianum*), which can be found in dry rocky soils of Southern and Western Europe and in some parts of the U.S., by methods well know to those skilled in the art (see, e.g., Wallace S. N. Extraction of nutraceuticals from milk thistle: part II. Extraction with organic solvents. *Appl Biochem Biotechnol.* 2003; 105–108:891–903; Barreto J. F. et al. Extraction of nutraceuticals from milk thistle: I. Hot water extraction. *Appl Biochem Biotechnol.* 2003; 105–108:881–9, each of which is incorporated by reference herein in its entirety). In a specific embodiment, the silymarin used in the compositions and methods of the present invention can be extracted from the seeds of the milk thistle plant by a two-step defatting and extraction process using organic solvents. In another specific embodiment, the silymarin used in the compositions and methods of the present invention can be extracted from the seeds of the milk thistle plant by defatting the seeds and extracting in ethanol at 85° C. and 100° C. In certain embodiments, at least 5%, 10%, 15%, 20%, 25%, 30%, 40%, 50%, 60%, 70%, 80%, 90%, 95% or more of milk thistle plant extract is silymarin. In a specific embodiment, at least 80% of milk thistle plant extract is silymarin.

In certain other embodiments, the silymarin used in the compositions and methods of the present invention can also be prepared from crude milk thistle seeds. In one embodiment, the seeds of the milk thistle plant can be processed, washed, dried, dehydrated, crushed, ground and/or frozen prior to isolating the silymarin. The seeds of the milk thistle plant can also be boiled in alcohol to make a silymarin solution. In a specific embodiment, about 5 g of milk thistle plant seeds can be boiled in about 500 ml of ethanol for 15 min to make a silymarin solution.

Alternatively, silymarin for use in the compositions and methods of the present invention is obtained by synthesizing one or more flavonoid molecules (e.g., silybin, silybinin A, silybinin B, silydianin, silychristin, and taxifolin), which can be synthesized by methods well known to those skilled in the art (see, e.g., Ahmed B. et al. Synthesis and antihepatotoxic activity of some heterocyclic compounds containing the 1,4-dioxane ring system. *Pharmazie.* 2003; 58(3):173–6; Guz N. R. et al. Synthesis and structures of regioisomeric hydnocarpin-type flavonolignans. *J Nat Prod.* 2000; 63(8): 1140–5; Tanaka H. et al. [Total synthesis of (+/−)-silybin, an antihepatotoxic flavonolignan] (in Japanese). *Chem Pharm Bull.* (Tokyo). 1985; 33(4):1419–23; Litkei G. Y. Synthesis of hypolipidemic silybin analog 3',4'-ethylenedioxyflavonoids. *Pharmazie.* 1984; 39(11):741–4, each of which is incorporated by reference herein in its entirety).

In another embodiment, the silymarin used in the compositions and methods of the present invention is purchased. Silymarin is commercially available in the form of a powder, solid, capsule, tablet, gel, solution, or emulsion. For example, silymarin can be purchased from companies such as Sigma Chemical Company (St. Louis, Mo., USA) or health and herb stores such as General Nutrition Centers, Inc. (Pittsburgh, Pa., USA). In a specific embodiment, the silymarin used in the compositions and methods of the present invention can be purchased from Vital Nutrients (Middletown, Conn., USA). In a more specific embodiment, the silymarin can be purchased from Vital Nutrients in 250 mg capsule units.

5.1.6 Lipoic Acid

Lipoic acid for use in the compositions and methods of the present invention can be prepared from food sources such as spinach, broccoli, beef, yeast (particularly Brewer's yeast), and certain organ meats (e.g., kidney, heart). In one embodiment, the food source can be processed, washed, dried, dehydrated, crushed, ground and/or frozen prior to isolating the lipoic acid.

Alternatively, the lipoic acid for use in the compositions and methods of the present invention can be synthesized by methods well known to those skilled in the art (see, e.g., Johnson M. G. et al. Synthesis of lipoic acid by *Streptococcus faecalis* 10C1 and end-products produced anaerobically from low concentrations of glucose. *J Gen Microbiol.* 1973; 78(1):47–55; Adger B. et al. The synthesis of (R)-(+)-lipoic acid using a monooxygenase-catalysed biotransformation as the key step. *Bioorg Med Chem.* 1997; 5(2):253–61; Self W. T. et al. Synthesis and characterization of selenotrisulfide-derivatives of lipoic acid and lipoamide. *Proc Natl Acad Sci USA.* 2000; 97(23):12481–6; Marquet A. et al. Biosynthesis of biotin and lipoic acid. *Vitam Horm.* 2001; 61:51–101, each of which is incorporated by reference herein in its entirety). In a specific embodiment, the lipoic acid used in the compositions and methods of the present invention has a molecular formula of $C_8H_{14}O_2S_2$ and a molecular weight of 206.3 g per mole. In another specific embodiment, the lipoic acid used in the compositions and methods of the present invention is alpha-lipoic acid.

In another embodiment, the lipoic acid used in the compositions and methods of the present invention is purchased. Lipoic acid is commercially available in the form of a powder, solid, capsule, tablet, gel, solution, or emulsion. For example, lipoic acid can be purchased from companies such as Sigma Chemical Company (St. Louis, Mo., USA) or health and herb stores such as General Nutrition Centers, Inc. (Pittsburgh, Pa., USA). In a specific embodiment, the lipoic acid used in the compositions and methods of the present invention can be purchased from Vital Nutrients (Middletown, Conn., USA). In a more specific embodiment, the lipoic acid can be purchased from Vital Nutrients in 150 mg capsule units.

5.1.7 D-alpha Tocopherol (Vitamin E)

D-alpha tocopherol is a fat-soluble vitamin that includes eight naturally occurring compounds in two classes designated as alpha-, beta-, gamma-, and delta-tocopherols and alpha-, beta-, gamma-, and delta-tocotrienols. In a specific embodiments, the d-alpha tocopherol used in the compositions and methods of the invention is mixed d-alpha-tocopherol. In a more specific embodiment, the mixed d-alpha-tocopherol comprises d-alpha tocopherol and mixed tocopherols including alpha-, beta-, gamma-, and delta-tocopherol.

Ascorbic acid for use in the compositions and methods of the present invention can be prepared from food sources such as vegetable oils, cereal grains, nuts, animal fats, meat, poultry, eggs, fruits, and green leafy vegetables. In one embodiment, the food source can be processed, washed, dried, dehydrated, crushed, ground and/or frozen prior to isolating the d-alpha-tocopherol.

Alternatively, d-alpha tocopherol for use in the compositions and methods of the invention can be synthesized and purified by methods well known to those skilled in the art (see, e.g., Saari C. A. et al. Synthesis and biological activity of sulfur analogs of a-tocopherol. *Int J Vitam Nutr Res.* 1971; 41(3):368–75; Saari C. A. et al. Synthesis and biological activity of selenium analogs of—tocopherol. *Int J Vitam Nutr Res.* 1971; 41(4):516–20; Asymmetric synthesis of natural vitamin E. Ka-kong Chan, Gabriel G Saucy assigned to Hoffmann-La Roche Inc. *Biotechnol Adv.* 1990; 8(3):663; Murase H. et al. Synthesis of a novel vitamin E derivative, 2-(alpha-D-glucopyranosyl) methyl-2,5,7,8-tetramethylchroman-6-ol, by alpha-glucosidase-catalyzed transglycosylation. *Lipids.* 1997; 32(1):73–8; Koga T. et al. Synthesis of a phosphatidyl derivative of vitamin E and its antioxidant activity in phospholipid bilayers. *Lipids.* 1994; 29(2):83–9; Zakharova E. I. et al. [Synthesis and antioxidative activity of structural analogs of vitamin E] (in Russian). *Bioorg Khim.* 1989; 15(9):1268–73, each of which is incorporated by reference herein in its entirety).

In another embodiment, the d-alpha tocopherol used in the compositions and methods of the present invention is purchased. D-alpha tocopherol is commercially available in the form of a powder, solid, capsule, tablet, gel, solution, or emulsion. For example, d-alpha tocopherol can be purchased from companies such as Sigma Chemical Company (St. Louis, Mo., USA) or health and herb stores such as General Nutrition Centers, Inc. (Pittsburgh, Pa., USA). In a specific embodiment, the d-alpha tocopherol used in the compositions and methods of the present invention can be purchased from Vital Nutrients (Middletown, Conn., USA). In a more specific embodiment, the d-alpha tocopherol can be purchased from Vital Nutrients in 400 iu capsule units.

5.1.8 Vitamin B-Complex

In certain embodiments, the vitamin B-complex for use in the compositions and methods of the invention comprises thiamine (B1), riboflavin (B2), niacin (B3), pantothenic acid (B5), pyridoxine (B6), biotin (B7 or H), folic acid (B9), and cyanocobalamin (B12). Vitamin B1 and B2 can be prepared from cereals and whole grains. Vitamin B1 can be prepared from potatoes, pork, seafood, liver, and kidney beans. Vitamin B2 can be prepared from enriched bread, dairy products, liver, and green leafy vegetables. Vitamin B3 can be prepared from liver, fish, chicken, lean red meat, nuts, whole grains, and dried beans. Vitamin B5 can be prepared from any food. Vitamin B6 can be prepared from fish, liver, pork, chicken, potatoes, wheat germ, bananas, and dried beans. Vitamin B7 or vitamin H can be prepared from peanuts, liver, egg yolks, bananas, mushrooms, watermelon, and grapefruit. Vitamin B9 can be prepared from green leafy vegetables, liver, citrus fruits, mushrooms, nuts, peas, dried beans, and wheat bread.

Alternatively, the vitamin B-complex for use in the compositions and methods of the invention can be synthesized and purified by methods well known to those skilled in the art (see, e.g., Kachan V. I. Synthesis of some vitamins of the vitamin B complex in *Bacillus polymyxa* Ross [in Ukrainian]. *Mikrobiol Zh.* 1970; 32(4):424–9; Isakova D. M. Synthesis of vitamin B groups by *Micrococcus* freudenreichii K-219 in carbohydrate and hydrocarbon nutrition media [in Ukrainia]. *Mikrobiol Zh.* 1975; 37(1):7–10; Kusaka T. Studies on vitamin B1 in the feces. 3. Synthesis of vitamin B1 by *Lactobacillus* and the effect of oral administration of *Lactobacillus* preparation on the quantity of vitamine B1 in the feces [in Japanese]. *Nippon Shonika Gakkai Zasshi.* 1967; 71(1):61–4; Kamogawa H. Synthesis of isoalloxazine polymer (vitamin B2 polymer). *J Polym Sci [A1].* 1969; 7(1):409–13; Kilburn J. Q. et al. Asparatic acid as a precursor for niacin synthesis by tubercle bacilli grown on 7H-10 agar medium. *Am J Clin Pathol.* 1968; 50(5): 582–6; Xia X. Q. Recent progress in synthesis of Vitamin B6 [in Chinese]. *Yao Xue Xue Bao.* 1964; 11(4):285–92; Jones T. H. et al. The biosynthesis of folic acid. VII. Enzymatic synthesis of pteridines from guanosine triphosphate. *J Biol Chem.* 1967; 242(18):3989–97; Woodward R. B. The total synthesis of vitamin B12. *Pure Appl Chem.* 1973; 33(1): 145–77; Sasaki T. et al. Synthesis of vitamin B 12 model compounds. *Bull Chem Soc Jpn.* 1969; 42(5):1308–16, each of which is incorporated by reference herein in its entirety).

In another embodiment, the vitamin B-complex used in the compositions and methods of the present invention is purchased. Vitamin B-complex is commercially available in the form of a powder, solid, capsule, tablet, gel, solution, or emulsion. For example, vitamin B-complex can be purchased from companies such as Sigma Chemical Company (St. Louis, Mo., USA) or health and herb stores such as General Nutrition Centers, Inc. (Pittsburgh, Pa., USA). In a specific embodiment, the vitamin B-complex used in the compositions and methods of the present invention can be purchased from Vital Nutrients (Middletown, Conn., USA).

5.2 Methods of Making the Compositions

The compositions of the present invention comprise one or more, or all of the antioxidants glycyrrhizin, *schisandra*, ascorbic acid, glutathione, silymarin, lipoic acid, d-alpha-tocopherol, and vitamin B-complex. In certain embodiments, the compositions can be for oral administration ("oral compositions") or can be administered parenterally ("parenteral compositions"), e.g., by infusion or intravenous injection. Each of the antioxidants in the compositions of the invention can be synthesized, purified, prepared and/or purchased as described above in Section 5.1 as an active ingredient, and can optionally contain a pharmaceutically acceptable carrier, filler, binder, excipient, and/or other ingredients provided that these materials do not significantly compromise the activities of the antioxidants. Other ingredients that can be incorporated into the compositions of the present invention, may include, but are not limited to, herbs (including traditional Chinese medicine products), herbal extracts, vitamins, amino acids, metal salts, metal chelates, coloring agents, flavor enhancers, preservatives, and the like.

In one embodiment, the antioxidants are enriched in the composition. In another embodiment, one or more, or all of the antioxidants are purified, e.g., so that the antioxidant preparation used in the compositions or methods of the invention is greater than 50%, 60%, 70%, 80%, 90%, 95%, 98%, or 99% by weight. In a specific embodiment, the antioxidant is at least 5%, at least 10%, at least 15%, at least 20%, at least 30%, at least 40%, at least 50%, at least 60%, at least 70%, at least 80%, at least 90%, at least 95%, at least 98%, or at least 99% purified.

According to the invention, the antioxidants, oral compositions and/or parenteral compositions can produce a healthful benefit in a subject with oxidative stress, lipid peroxidation, chronic liver disease, chronic HCV infection and/or NASH.

5.2.1 Formulation of the Oral Compositions

The oral compositions of the invention comprises one or more, or all of the antioxidants glycyrrhizin, *schisandra* extract, ascorbic acid, glutathione, silymarin, lipoic acid, and d-alpha-tocopherol. In certain embodiments, the oral composition comprises glycyrrhizin, *schisandra*, ascorbic acid, glutathione, silymarin, lipoic acid, and d-alpha-tocopherol. In certain other embodiments, each oral composition comprises only one antioxidant selected from the group consisting of glycyrrhizin, *schisandra* extract, ascorbic acid, glutathione, silymarin, lipoic acid, and d-alpha-tocopherol. In certain other embodiments, each oral composition comprises one or more, but not all of the antioxidants glycyrrhizin, *schisandra* extract, ascorbic acid, glutathione, silymarin, lipoic acid, and d-alpha-tocopherol.

In a specific embodiment, the compositions consist essentially of the antioxidants specified herein.

As used herein, the term "about" is intended to encompass standard experimental error.

In a specific embodiment, the oral composition comprises about 25 mg, 50 mg, 100 mg, 200 mg, 250 mg, 300 mg, 400 mg, 500 mg, 600 mg, 700 mg, 800 mg, 900 mg, 1,000 mg, 1,100 mg, 1,200 mg, 1,300 mg, 1,400 mg, 1,500 mg, 1,600 mg, 1,700 mg, 1,800 mg, 1,900 mg, or 2,000 mg of glycyrrhizin. Preferably, the oral composition comprises about 1,000 mg of glycyrrhizin.

In a specific embodiment, the oral composition comprises about 25 mg, 50 mg, 100 mg, 200 mg, 300 mg, 400 mg, 500 mg, 600 mg, 700 mg, 800 mg, 900 mg, 1,000 mg, 1,100 mg, 1,200 mg, 1,300 mg, 1,400 mg, 1,500 mg, 1,600 mg, 1,700 mg, 1,800 mg, 1,900 mg, 2,000 mg, 2,100 mg, 2,200 mg, 2,300 mg, 2,400 mg, 2,500 mg, 2,600 mg, 2,700 mg, 2,800 mg, 2,900 mg, 3,000 mg, 3,500 mg, or 4,000 mg of *schisandra*. Preferably, the oral composition comprises about 1,500 mg of *schisandra*.

In a specific embodiment, the oral composition comprises about 25 mg, 50 mg, 100 mg, 200 mg, 300 mg, 400 mg, 500 mg, 600 mg, 700 mg, 800 mg, 900 mg, 1,000 mg, 1,100 mg, 1,200 mg, 1,300 mg, 1,400 mg, 1,500 mg, 1,600 mg, 1,700 mg, 1,800 mg, 1,900 mg, 2,000 mg, 2,500 mg, 3,000 mg, 4,000 mg, 5,000 mg, 6,000 mg, 7,000 mg, 8,000 mg, 9,000 mg, 10,000 mg, 15,000 mg, or 20,000 mg of ascorbic acid. Preferably, the oral composition comprises about 6,000 mg of ascorbic acid.

In a specific embodiment, the oral composition comprises about 10 mg, 20 mg, 30 mg, 40 mg, 50 mg, 75 mg, 100 mg, 125 mg, 150 mg, 200 mg, 250 mg, 300 mg, 400 mg, 500 mg, 600 mg, 700 mg, 800 mg, 900 mg, 1,000 mg, 1,100 mg, 1,200 mg, 1,300 mg, 1,400 mg, or 1,500 mg of glutathione. Preferably, the oral composition comprises about 300 mg of glutathione.

In a specific embodiment, the oral composition comprises about 1 mg, 5 mg, 10 mg, 20 mg, 30 mg, 40 mg, 50 mg, 75 mg, 100 mg, 125 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,100 mg, 1,150 mg, 1,200 mg, 1,250 mg, 1,300 mg, 1,400 mg, or 1,500 mg of silymarin. Preferably, the oral composition comprises about 750 mg of silymarin.

In a specific embodiment, the oral composition comprises about 1 mg, 5 mg, 10 mg, 20 mg, 30 mg, 40 mg, 50 mg, 75 mg, 100 mg, 125 mg, 150 mg, 200 mg, 250 mg, 300 mg, 350 mg, 400 mg, 450 mg, or 500 mg of lipoic acid. Preferably, the oral composition comprises about 300 mg of lipoic acid.

In a specific embodiment, the oral composition comprises about 25 iu, 50 iu, 100 iu, 200 iu, 300 iu, 400 iu, 500 iu, 600 iu, 700 iu, 800 iu, 900 iu, 1,000 iu, 1,100 iu, 1,200 iu, 1,300 iu, 1,400 iu, 1,500 iu, 1,600 iu, 1,700 iu, 1,800 iu, 1,900 iu, 2,000 iu of d-alpha-tocopherol. Preferably, the oral composition comprises about 800 iu of d-alpha-tocopherol.

In a specific embodiment, the oral composition comprises about 1,000 mg of glycyrrhizin, about 1,500 mg of *schisandra*, about 6,000 mg of ascorbic acid, about 300 mg of glutathione, about 750 mg of silymarin, about 300 mg of lipoic acid, and about 800 iu of d-alpha-tocopherol.

Dosage forms include tablets, capsules, gel, dispersions, suspensions, solutions, and the like. In one embodiment, the oral composition or each antioxidant/ingredient in the oral composition may be presented as discrete units such as capsules, cachets, or tablets, each containing a predetermined amount of the oral compositions. In another embodiment, the oral composition or each antioxidant/ingredient in the oral compositions may be presented as a powder or granules or as a solution or a suspension in an aqueous liquid, a non-aqueous liquid, an oil-in-water emulsion, or a water-in-oil liquid emulsion. In yet another embodiment, the oral composition is prepared by uniformly and intimately admixing the one or more antioxidants/ingredients with liquid carriers or finely divided solid carriers or both, and then, if necessary, shaping the product into the desired presentation. Such products can be used as pharmaceuticals or dietary supplements, depending on the dosage and circumstances of its use.

The oral compositions of the present invention may additionally include binding agents (e.g., pregelatinized maize starch, polyvinylpyrrolidone or hydroxypropyl methylcellulose); binders or fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets or capsules can be coated by methods well known in the art.

Generally, because of their ease of administration, tablets and capsules represent the most advantageous oral dosage unit form, in which case solid pharmaceutical carriers as described above are employed. In a preferred embodiment, the composition is a capsule. The capsules can be formulated by any commercially available methods. In certain embodiments, the oral composition is a capsule containing 50 mg, 100 mg, 150 mg, 200 mg, 250 mg, 300 mg, 400 mg, 500 mg, 1,000 mg, 1,500 mg, 2,000 mg, 2,500 mg, 3,000 mg, 5,000 mg, 10,000 mg, 20,000 mg, or more of the antioxidant in powder form. The number of capsules to be taken each day to obtain the total daily dose in a subject depends on the amount of antioxidant contained within each capsule. For example, a capsule may comprise about 500 mg of glycyrrhizin powder. To achieve a total daily dose of about 1,000 mg per day, a subject can take one capsule at a time for two times per day or two capsules once a day.

Liquid preparations of the oral compositions can take the form of, for example, solutions, syrups or suspensions, or they can be presented as a dry product for constitution with water or other suitable vehicle before use. The temperature of the liquid used to reconstitute the dried product should be less than 65° C. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). As described below, the preparations can also be made to resemble foods or beverages, containing buffer salts, flavoring, coloring and sweetening agents as appropriate. The oral composition can be formulated as a health drink and packaged in liquid containers, each containing a predetermined amount of the antioxidants. Standard methods of quality control and packaging are applied to produce in one embodiment of the invention, the oral compositions are packaged in 10 ml, 20 ml, 30 ml, 40 ml, 50 ml, 75 ml, 100 ml, 150 ml, 200 ml, 250 ml, 500 ml, 750 ml, or 1,000 ml liquid containers. The number of liquid containers to be taken each day to obtain the total daily dose of the oral compositions in a subject depends on the amount of oral compositions contained within each container. For example, a liquid container may comprise about 250 mg of glycyrrhizin powder. To achieve a total daily dose of about 1,000 mg per day, a subject can drink four liquid containers per day.

In another embodiment, the oral compositions can be added directly to foods so that an effective amount of antioxidant therein is ingested during normal meals. Any methods known to those skilled in the art may be used to add to or incorporate the oral compositions into natural or processed foods, provided that the antioxidants therein remain active. Preferably, the nutritional compositions of the invention are made and stored under conditions, such as temperature, from about 0° C. to 4° C. As used herein, the term "food" broadly refers to any kind of material, liquid or solid, that is used for nourishing an animal, and for sustaining normal or accelerated growth of an animal including humans. Many types of food products or beverages, such as but not limited to, fruit juice, herbal extracts, tea-based beverages, dairy products, soybean product (e.g., tofu), and rice products, can be used to form nutritional compositions comprising the oral compositions of the invention.

5.2.2 Formulation of the Parenteral Compositions

The parenteral compositions of the invention comprises one or more, or all of the antioxidants glycyrrhizin, ascorbic acid, glutathione, and B-complex. In certain embodiments, the parenteral composition comprises glycyrrhizin, ascorbic acid, glutathione, and B-complex. In certain other embodiments, each parenteral composition comprises only one antioxidant selected from the group consisting of glycyrrhizin, ascorbic acid, glutathione, and B-complex. In certain other embodiments, each parenteral composition comprises one or more, but not all of the antioxidants glycyrrhizin, ascorbic acid, glutathione, and B-complex.

In a specific embodiment, the compositions consist essentially of the antioxidants specified herein.

As used herein, the term "about" is intended to encompass standard experimental error.

In a specific embodiment, the parenteral composition comprises about 5 mg, 10 mg, 15 mg, 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 200 mg, or 300 mg of glycyrrhizin. Preferably, the parenteral composition comprises about 120 mg of glycyrrhizin.

In a specific embodiment, the parenteral composition comprises 100 mg, 200 mg, 300 mg, 400 mg, 500 mg, 600 mg, 700 mg, 800 mg, 900 mg, 1,000 mg, 1,100 mg, 1,200 mg, 1,300 mg, 1,400 mg, 1,500 mg, 1,600 mg, 1,700 mg, 1,800 mg, 1,900 mg, 2,000 mg, 2,500 mg, 3,000 mg, 4,000 mg, 5,000 mg, 6,000 mg, 7,000 mg, 8,000 mg, 9,000 mg, 10,000 mg, 15,000 mg, or 20,000 mg of ascorbic acid. Preferably, the parenteral composition comprises about 10,000 mg of ascorbic acid.

In a specific embodiment, the parenteral composition comprises about 10 mg, 20 mg, 30 mg, 40 mg, 50 mg, 75 mg, 100 mg, 125 mg, 150 mg, 200 mg, 250 mg, 300 mg, 400 mg, 500 mg, 600 mg, 700 mg, 800 mg, 900 mg, 1,000 mg, 1,100 mg, 1,200 mg, 1,300 mg, 1,400 mg, or 1,500 mg of glutathione. Preferably, the parenteral composition comprises about 750 mg of glutathione.

In a specific embodiment, the parenteral composition comprises about 0.01 ml, 0.05 ml, 0.1 ml, 0.2 ml, 0.3 ml, 0.5 ml, 1.0 ml, 1.5 ml, 2.0 ml, 3.0 ml, 5.0 ml, or 10.0 ml of vitamin B-complex. Preferably, the parenteral composition comprises about 1.0 ml of vitamin B-complex.

In a specific embodiment, the parenteral composition comprises about 120 mg of glycyrrhizin, about 10,000 mg of ascorbic acid, about 750 mg of glutathione, and about 1.0 ml of vitamin B-complex.

In preferred embodiments, each antioxidant in the parenteral compositions of the invention can be mixed with sterile water or normal saline for parenteral administration, e.g., by infusion or intravenous injection. When a parenteral composition comprises more than one antioxidant, each antioxidant can be individually mixed with sterile water or normal saline and then mix together, or each antioxidant can be mixed together prior to being mixed with sterile water or normal saline.

Methods of administering the parenteral compositions of the invention include, but are not limited to, parenteral (e.g., subcutaneous, intramuscular, intraorbital, intracapsular, intraspinal, intrasternal, intravenous, intradermal, intraperitoneal, intraportal), epidural, and mucosal (e.g., intranasal) administration. In a specific embodiment, the parenteral compositions are parenterally administered to a subject. In another specific embodiment, the parenteral compositions are administered to a subject parenterally, by infusion. In another specific embodiment, the parenteral compositions are administered to a subject parenterally, by injection, preferably by intravenous injection.

Where the parenteral composition is to be administered by infusion, it can be dispensed with an infusion bottle containing sterile pharmaceutical grade water or saline. Where the composition is administered parenterally, preferably by infusion, an ampoule of sterile water or saline can be provided so that the ingredients may be mixed prior to administration.

5.2.3 Kits

In certain embodiments, one or more of the antioxidants, oral compositions and/or parenteral compositions of the invention are supplied in a kit. In one embodiment, the kit comprises one or more of the antioxidants glycyrrhizin, *schisandra* extract, ascorbic acid, L-glutathione, silymarin, lipoic acid, d-alpha-tocopherol, and vitamin B-complex. In one embodiment, the kit comprises a first container comprising an oral composition comprising glycyrrhizin, *schisandra* extract, ascorbic acid, L-glutathione, silymarin, lipoic acid, and d-alpha-tocopherol. In another embodiment, the kit comprises a first container containing a parenteral composition comprising glycyrrhizin, ascorbic acid, L-glutathione, and vitamin B-complex. In another embodiment, the kit comprises a first container comprising an oral composition comprising glycyrrhizin, *schisandra* extract, ascorbic acid, L-glutathione, silymarin, lipoic acid, and d-alpha-tocopherol, and a second container comprising a parenteral composition comprising glycyrrhizin, ascorbic acid, L-glutathione, and vitamin B-complex.

In another embodiment, the kit comprises a first container comprising a first oral composition comprising a first antioxidant, a second container comprising a second oral composition comprising a second antioxidant, a third container comprising a third oral composition comprising a third antioxidant, a fourth container comprising a fourth oral composition comprising a fourth antioxidant, a fifth container comprising a fifth oral composition comprising a fifth antioxidant, a sixth container comprising a sixth oral composition comprising a sixth antioxidant, and a seventh container comprising a seventh oral composition comprising a seventh antioxidant. In another embodiment, the kit comprises a first container comprising a first parenteral composition comprising a first antioxidant, a second container comprising a second parenteral composition comprising a second antioxidant, a third container comprising a third parenteral composition comprising a third antioxidant, a fourth container comprising a fourth parenteral composition comprising a fourth antioxidant. In another embodiment, the kit comprises a first container comprising a first oral composition comprising a first antioxidant, a second container comprising a second oral composition comprising a second antioxidant, a third container comprising a third oral composition comprising a third antioxidant, a fourth container comprising a fourth oral composition comprising a fourth antioxidant, a fifth container comprising a fifth oral composition comprising a fifth antioxidant, a sixth container comprising a sixth oral composition comprising a sixth antioxidant, and a seventh container comprising a seventh oral composition comprising a seventh antioxidant, an eighth container comprising a first parenteral composition comprising an eighth antioxidant, a ninth container comprising a second parenteral composition comprising a ninth antioxidant, a tenth container comprising a third parenteral composition comprising a tenth antioxidant, and an eleventh container comprising a fourth parenteral composition comprising an eleventh antioxidant. Each of the oral composition and/or parenteral composition may comprise the same or different antioxidant.

In a specific embodiment, the kit comprises a first container comprising a first oral composition comprising glycyrrhizin, a second container comprising a second oral composition comprising *schisandra* extract, a third container comprising a third oral composition comprising ascorbic acid, a fourth container comprising a fourth oral composition comprising L-glutathione, a fifth container comprising a fifth oral composition comprising silymarin, a sixth container comprising a sixth oral composition comprising lipoic acid, and a seventh container comprising a seventh oral composition comprising d-alpha-tocopherol. In another specific embodiment, the kit comprises a first container comprising a first parenteral composition comprising glycyrrhizin, a second container comprising a second parenteral composition comprising ascorbic acid, a third container comprising a third parenteral composition comprising L-glutathione, a fourth container comprising a fourth parenteral composition comprising vitamin B-complex. In another specific embodiment, the kit comprises a first container comprising a first oral composition comprising glycyrrhizin, a second container comprising a second oral composition comprising *schisandra* extract, a third container comprising a third oral composition comprising ascorbic acid, a fourth container comprising a fourth oral composition comprising L-glutathione, a fifth container comprising a fifth oral composition comprising silymarin, a sixth container comprising a sixth oral composition comprising lipoic acid, a seventh container comprising a seventh oral composition comprising d-alpha-tocopherol, an eighth container comprising a first parenteral composition comprising glycyrrhizin, a ninth container comprising a second parenteral composition comprising ascorbic acid, a tenth container comprising a third parenteral composition comprising L-glutathione, an eleventh container comprising a fourth parenteral composition comprising vitamin B-complex.

In one embodiment, each container comprises each oral composition in a unit dosage form, for example, as a solid, capsule, tablet, gel, etc. In one embodiment, each container comprises each parenteral composition in a unit dosage form, for example, as a dry lyophilized powder or water free concentrate in a hermetically sealed container such as an ampoule or sachette indicating the quantity of active agent. In kits comprising the parenteral composition of the invention, the kit further comprises a needle or syringe, preferably packaged in sterile form, for injecting the parenteral composition, and/or a packaged alcohol pad. Instructions are optionally included for administration of the compositions of the invention by a clinician or by the patient.

5.3 Methods of Using the Compositions

The present invention further provides methods of using the antioxidants and compositions of the invention. In one embodiment, the antioxidants and compositions are used to reduce oxidative stress and/or lipid peroxidation. In another embodiment, the antioxidants and compositions are used to treat or prevent chronic liver disease, chronic HCV infection, and/or NASH. The methods comprise administering an effective amount of the antioxidants and/or compositions to a subject in need. As used herein, the term "an effective amount" means an amount sufficient to reduce oxidative stress or lipid peroxidation, or treat or prevent chronic liver disease, chronic HCV infection or NASH and/or provide a therapeutic or healthful benefit in the context of reducing the level of free oxygen radicals, increasing the level of antioxidants, reducing the levels of adducts, normalizing liver enzymes, reducing viral load, improving liver histology (e.g., cirrhosis, fibrosis, lobular hepatitis, periportal bridging necrosis), and/or improving quality of life (e.g., general health, physical health, emotional health) in a subject.

In a specific embodiment, the method comprises orally administering to a subject glycyrrhizin, *schisandra*, ascorbic acid, glutathione, silymarin, lipoic acid, and d-alpha-tocopherol in amounts together effective to reduce oxidative stress or lipid peroxidation, and/or treat or prevent chronic liver disease, chronic HCV infection or NASH. In another specific embodiment, the method comprises parenterally administering to the subject glycyrrhizin, ascorbic acid, glutathione, and vitamin B-complex in amounts together effective to reduce oxidative stress or lipid peroxidation, and/or treat or prevent chronic liver disease, chronic HCV infection or NASH. In another specific embodiment, the method comprises orally administering to the subject glycyrrhizin, *schisandra*, ascorbic acid, glutathione, silymarin, lipoic acid, and d-alpha-tocopherol, and parenterally administering to the subject glycyrrhizin, ascorbic acid, glutathione, and vitamin B-complex in amounts together effective to reduce oxidative stress or lipid peroxidation, and/or treat or prevent chronic liver disease, chronic HCV infection or NASH. In yet another specific embodiment, the method comprises administering orally to the subject a first oral composition comprising glycyrrhizin, a second oral composition comprising *schisandra*, a third oral composition comprising ascorbic acid, a fourth oral composition comprising glutathione, a fifth oral composition comprising silymarin, a sixth oral composition comprising lipoic acid, and a seventh oral composition comprising d-alpha-tocopherol, in amounts together effective to reduce oxidative stress or lipid peroxidation, and/or treat or prevent chronic liver disease, chronic HCV infection or NASH. In yet another specific embodiment, the method comprises parenterally administering to a subject a first parenteral composition comprising glycyrrhizin, a second parenteral composition comprising ascorbic acid, a third parenteral composition comprising glutathione, and a fourth parenteral composition comprising vitamin B-complex, in amounts together effective to reduce oxidative stress or lipid peroxidation, and/or treat or prevent chronic liver disease, chronic HCV infection or NASH. In yet another specific embodiment, the method comprises orally administering to a subject first oral composition comprising glycyrrhizin, a second oral composition comprising *schisandra* extract, a third oral composition comprising ascorbic acid, a fourth oral composition comprising glutathione, a fifth oral composition comprising silymarin, a sixth oral composition comprising lipoic acid, a seventh oral composition comprising d-alpha-tocopherol, and parenterally administering to the subject a first parenteral composition comprising glycyrrhizin, a second parenteral composition comprising ascorbic acid, a third parenteral composition comprising glutathione, and a fourth parenteral composition comprising vitamin B-complex, in amounts together effective to reduce oxidative stress or lipid peroxidation, and/or treat or prevent chronic liver disease, chronic HCV infection or NASH.

The effective amount will vary with the subject treated. As used herein, the terms "subject" and "patient" are used interchangeably. The subject can be an animal, preferably a mammal including a non-primate (e.g., a cow, pig, horse, cat, dog, rat, and mouse) and a primate (e.g., a monkey, such as a cynomolgous monkey, chimpanzee, and a human), and more preferably a human.

In certain embodiments, the subject is a mammal, preferably a human. In one embodiment, the subject is a human infant or a human infant born prematurely. In another embodiment, the subject is a human child or a human adult. In yet another embodiment, the subject is an elderly human. As used herein, the term "human infant" refers to a human less than 24 months, preferably less than 16 months, less than 6 months, less than 3 months, less than 2 months, or less than 1 month of age. As used herein, the term "human child" refers to a human between 24 months of age and 18 years of age. As used herein, the term "human adult" refers to a human 18 years of age or older. As used herein, the term "elderly human" refers to a human 55 years of age or older.

In another embodiment, the subject is a subject with chronic liver disease. In a specific embodiment, the subject is a subject with chronic HCV infection. In another specific embodiment, the subject is a subject with NASH. In another embodiment, the subject is a human at risk of developing chronic liver disease, chronic HCV infection or NASH. In another embodiment, the subject is a subject suffering from oxidative stress and/or lipid peroxidation. In another embodiment, the subject is immunocompromised or immunosuppressed.

In a specific embodiment, a subject with chronic liver disease is a human with cirrhosis of the liver. In another specific embodiment, a subject with chronic liver disease is a human with fibrosis of the liver.

In a specific embodiment, chronic HCV infection is manifested by raised liver enzymes (e.g., ALT, AST), persistent (e.g., greater than six months) HCV RNA levels, and/or histological evidence of liver damage, fibrosis, and/or cirrhosis.

In a specific embodiment, NASH is manifested by raised liver enzymes (e.g., ALT and AST), pathological evidence of steatosis (fatty liver), fibrosis, and/or cirrhosis.

As used herein, the phrase "a subject suffering from oxidative stress and/or lipid peroxidation" refers to a subject with higher than normal levels of reactive oxygen species (ROS), higher than normal levels of adducts, and/or lower than normal level of antioxidants in the tissue, blood, serum, cells, and/or plasma.

In certain embodiments, the subject can be receiving concurrently other therapies against oxidative stress, lipid peroxidation, chronic liver disease, chronic HCV infection, and/or NASH. In one embodiment, the subject can be a subject who had undergone a regimen of treatment (e.g., antioxidants, interferon, ribavirin, liver transplantation) and whose liver damage is regressing. In another embodiment, the subject can be a subject who had undergone a regimen of treatment and who appears to be clinically free of the virus and/or steatosis. The antioxidants, oral compositions and/or parenteral compositions of the invention can be administered adjunctively with any of the conventional treatment modalities, such as but not limited to antiviral therapy and/or surgery. In one embodiment, the antioxidants, oral compositions and/or parenteral compositions of the invention can be administered to a subject to reduce the probability of relapse after a successful course of treatment.

In certain other embodiments, the subject can be one who has not yet been diagnosed with chronic liver disease, chronic HCV infection or NASH but is predisposed to or at high risk of developing chronic liver disease, chronic HCV infection or NASH as a result of genetic factors and/or environmental factors. The subject may also be one who displays characteristics that are associated with a high risk of chronic liver disease, chronic HCV infection or NASH, such as suspect cells in biopsy and/or body fluids (e.g., tissue, blood, serum, cells, plasma).

The therapeutically effective dose for the subject will also vary with the condition to be treated and the severity of the condition to be treated. The dose, and perhaps the dose frequency, can also vary according to the age, gender, body weight, and response of the individual subject.

As used herein, the term "therapeutically effective amount" refers to that amount of the antioxidant or composition sufficient to reduce oxidative stress or lipid peroxidation, and/or treat, manage, or ameliorate chronic liver disease, chronic HCV infection or NASH or the symptoms or histopathology associated with chronic liver disease, chronic HCV infection or NASH. A therapeutically effective amount may refer to the amount of antioxidant or composition sufficient to reduce the level of reactive oxygen species, increase the level of antioxidants, reduce the level of adducts, reduce the level or extent of cirrhosis, fibrosis, lobular hepatitis, and/or perioportal bridging necrosis, reduce the level of liver enzymes, reduce viral load, improve liver histology, and/or improve quality of life in a subject. A therapeutically effective amount may also refer to the amount of the antioxidant or composition that provides a therapeutic benefit in the treatment or management of the symptoms or histopathology associated with chronic liver disease, chronic HCV infection or NASH. Further, a therapeutically effective amount with respect to an antioxidant or composition of the invention means that amount of the antioxidant or composition alone, or in combination with other therapies, that provides a therapeutic benefit in the treatment, management, or amelioration of chronic liver disease, chronic HCV infection or NASH or the symptoms or histopathology associated with chronic liver disease, chronic HCV infection or NASH.

Symptoms of chronic liver disease include, but are not limited to, cirrhosis and fibrosis. Symptoms of chronic HCV infection include, but are not limited to, stomach pain, fever, joint pain, raised liver enzymes (e.g., ALT, AST), persistent (e.g., greater than six months) HCV RNA levels, and/or histological evidence of liver damage, fibrosis, and/or cirrhosis. Symptoms of NASH include, but are not limited to, occasional, vague right upper-quadrant abdominal pain (below the rib-cage on the right side), raised liver enzymes (e.g., ALT and AST), pathological evidence of steatosis (fatty liver), fibrosis, and/or cirrhosis. Symptoms of cirrhosis include, but are not limited to, abnormal nerve function, ascites (build-up of fluid in the abdominal cavity), breast enlargement in men, coughing up or vomiting blood, curling of fingers (Dupuytren contracture of the palms), gallstones, hair loss, itching, jaundice, kidney failure, liver encephalopathy, muscle loss, poor appetite, portal hypertension, redness of palms, salivary gland enlargement in cheeks, shrinking of testes, small spider-like veins in skin, weakness, weight loss, spider angiomas (a central arteriole from which numerous small branching vessels radiate), jaundice (yellowish discoloration of the skin), pruritus (itching), gynecomastia (enlargement of the male breast), ascites (an effusion and accumulation of serous fluid in the abdominal cavity), encephalopathy, and asterixis (flapping tremor).

As used herein, the terms "treat," "treating" and "treatment" with respect to chronic liver disease, chronic HCV infection or NASH refer to reducing or eliminating chronic liver disease, chronic HCV infection or NASH, respectively, or the symptoms or histopathology associated with chronic liver disease, chronic HCV infection or NASH, respectively. In specific embodiments, the terms encompass the reduction of the level of reactive oxygen species, increase in the level of antioxidants, reduce the level of adducts, reduction of the extent of cirrhosis, fibrosis, lobular hepatitis, and/or periportal bridging necrosis, reduction of liver enzymes, reduction of viral load, improvement of liver histology, and/or improvement of quality of life of a subject with chronic liver disease, chronic HCV infection or NASH.

In certain embodiments, a prophylactically effective amount of the composition is administered to the subject to prevent oxidative stress or lipid peroxidation, or to prevent the development of chronic liver disease, chronic HCV infection or NASH.

As used herein, the term "prophylactically effective amount" refers to that amount of the antioxidant or composition sufficient to prevent chronic liver disease, chronic HCV infection or NASH or the symptoms or histopathology associated with chronic liver disease, chronic HCV infection or NASH. A prophylactically effective amount may refer to the amount of antioxidant or composition sufficient to reduce the level of reactive oxygen species, increase the level of antioxidants, reduce the level of adducts, reduce the extent of cirrhosis, fibrosis, lobular hepatitis, and/or periportal bridging necrosis, reduce the level of liver enzymes, reduce viral load, improve liver histology, and/or improve quality of life in a subject with chronic liver disease, chronic HCV infection or NASH.

As used herein, the terms "prevent," "preventing" and "prevention" with respect to chronic liver disease, chronic HCV infection or NASH refer to the prevention of chronic liver disease, chronic HCV infection or NASH, respectively, or the symptoms or histopathology associated with chronic liver disease, chronic HCV infection or NASH, respectively.

In a preferred embodiment, the total daily dose range of the antioxidant or oral composition for a subject with chronic liver disease, chronic HCV infection or NASH, is in the range of 500 to 1,500 mg, preferably 1,000 mg glycyrrhizin; 1,000 to 3,000 mg, preferably 1,500 mg *schisandra;* 500 to 10,000 mg, preferably 6,000 mg ascorbic acid; 50 to 1,000 mg, preferably 300 mg glutathione; 80 to 1,000 mg, preferably 750 mg silymarin; 100 to 1,200 mg, preferably 300 mg lipoic acid; and 200 to 1,600 iu, preferably 800 iu d-alpha-tocopherol, administered in single or divided doses.

In another preferred embodiment where the antioxidant or parenteral composition is given semi-weekly (twice a week), the total weekly dose range of the antioxidant or parenteral composition for a subject with chronic liver disease, chronic HCV infection or NASH, is in the range of 10 to 500 mg, preferably 120 mg glycyrrhizin; 1,000 to 20,000 mg, preferably 10,000 mg ascorbic acid; 250 to 1,500 mg, preferably 750 mg glutathione; and 0.1 to 100 ml, preferably 1 ml vitamin B-complex, administered in single or divided doses. It may be necessary to use dosages outside these ranges in some cases as will be apparent to those skilled in the art.

In certain embodiments, one or more oral compositions is/are administered prior to the administration of one or more parenteral compositions. In certain other embodiments, one or more oral compositions is/are administered after the administration of one or more parenteral compositions. In preferred embodiments, one or more oral compositions and one or more parenteral compositions are administered to a subject at the same time.

In certain embodiments, one or more antioxidants is/are administered sequentially. In certain other embodiments, one or more antioxidants is/are administered simultaneously.

In one embodiment, one or more compositions comprising glycyrrhizin, *schisandra* extract, ascorbic acid, L-glutathione, silymarin, lipoic acid, and d-alpha-tocopherol is/are administered orally to a subject prior to parenterally administering to the subject one or more compositions comprising glycyrrhizin, ascorbic acid, L-glutathione, and vitamin B-complex. In another specific embodiment, one or more compositions comprising glycyrrhizin, *schisandra* extract, ascorbic acid, L-glutathione, silymarin, lipoic acid, and d-alpha-tocopherol is/are administered orally to a subject after parenterally administering to the subject one or more compositions comprising glycyrrhizin, ascorbic acid, L-glutathione, and vitamin B-complex. In preferred embodiments, one or more compositions comprising glycyrrhizin, *schisandra* extract, ascorbic acid, L-glutathione, silymarin, lipoic acid, and d-alpha-tocopherol is/are administered orally to a subject at the same time that one or more compositions comprising glycyrrhizin, ascorbic acid, L-glutathione, and vitamin B-complex is/are parenterally administering to the subject, e.g., by infusion or intravenous injection.

The length of time for a course of treatment can be at least 1 week, at least 2 weeks, at least 3 weeks, at least 4 weeks, at least 5 weeks, at least 7 weeks, at least 10 weeks, at least 13 weeks, at least 15 weeks, at least 20 weeks, at least 6 months, or at least 1 year. In certain embodiments, the antioxidants, oral compositions and parenteral compositions can be administered for a period of time until the symptoms and/or infection of the patients by the viruses are under control, or when the disease has regressed partially or completely.

The levels of reactive oxygen species, antioxidants, and/or adducts, liver chemistries, viral load, liver histology, and/or general health, physical health, and/or emotional health of the subjects after treatment can be measured at 1 week, 2 weeks, 3 weeks, 4 weeks, 5 weeks, 10 weeks, 15 weeks, 20 weeks, 30 weeks, 40 weeks, or a year of posttreatment. Doctor's visits can take place before, during, and/or after the course of treatment, for example, on a daily, weekly, bi-weekly, monthly, or yearly basis.

In a specific embodiment, the antioxidants and compositions can be administered as a dietary supplement for as long as 6 months, or in accordance with recommended length of use under the Dietary Supplement Health and Education Act (DSHEA) or other government or industry guidelines. Further, it is noted that the nutritionist, dietician, clinician or treating physician will know how and when to interrupt, adjust, or terminate use of the antioxidants and compositions as a medicament or dietary supplement in conjunction with individual patient response.

The effects of the antioxidants, oral compositions and parenteral compositions of the invention on the development and progression of oxidative stress, lipid peroxidation, chronic liver disease or disorder, chronic HCV infection and NASH can be monitored by any methods known to one skilled in the art, including but not limited to measuring: a) changes in levels of reactive oxygen species; b) changes in levels of antioxidants; c) changes in levels of adducts; b) changes in liver enzymes; c) changes in viral load; d) changes in liver histology; and e) changes in quality of life of a subject.

5.3.1 Methods of Reducing Oxidative Stress and/or Lipid Peroxidation in a Subject The invention relates to methods of reducing oxidative stress and/or lipid peroxidation in a subject comprising administering to the subject an effective amount of one or more antioxidants and/or compositions of the invention.

A reduction of oxidative stress or lipid peroxidation in a subject can be determined, for example, by measuring the levels of spin-trapped reactive oxygen species (measure of free oxygen radicals themselves), antioxidants (measure of scavenger depletion), 8-hydroxy-2'-deoxyguanosine (measure of DNA damage), and adducts. Other methods of measuring oxidative stress are known to those skilled in the art (see, e.g., Van Hoom E. C. et al. A fast and accurate method to measure both oxidative stress and vitality in a single organ slice. *Anal Biochem.* 2003; 320(1):82–7; Franklin R. A. The use of the yeast two-hybrid system to measure protein-protein interactions that occur following oxidative stress. *Methods Mol Biol.* 2003; 218:47–57; Coolen S. A. et al. A new method for measuring oxidative stress in claudicants during strenuous exercise using free radical derivatives of antipyrine as indicators: a pilot study. *Ann Clin Lab Sci.* 2002; 32(2):181–7).

In certain embodiments, the level of reactive oxygen species, antioxidants, and adducts can be measured in a biological material from the subject (e.g., tissue, blood, serum, cells, plasma).

In a specific embodiment, the invention provides a method for reducing the level of reactive oxygen species in a subject comprising administering to the subject a therapeutically effective amount or a prophylactically effective amount of one or more of the oral compositions and/or parenteral compositions of the invention. Methods for measuring the level of reactive oxygen species are well known in the art (see, e.g., Ohoi I. et al. A simple chemiluminescence method for measuring oxygen-derived free radicals generated in oxygenated rat myocardium. *Jpn J Pharmacol* (Tokyo). 1993; 61(2):101–7; Charlon V. et al. [Perspectives of in-situ measuring of oxygen free radicals] (in French). *Ann Cardiol Angeiol* (Paris). 1986; 35(7 Pt 2):432–4, each of which is incorporated by reference herein in its entirety). In one embodiment, the level of reactive oxygen species in the tissue, blood, serum, cells, plasma of a subject is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

In another specific embodiment, the invention provides a method for increasing the level of antioxidants in a subject comprising administering to the subject a therapeutically effective amount or a prophylactically effective amount of one or more of the oral compositions and/or parenteral compositions of the invention. Methods for measuring the level of antioxidants are well known in the art (see, e.g., Teselkin IuO. [The measuring of blood plasma antioxidant activity by the hemoglobin-hydrogen peroxide-luminol system] (in Russian). *Vopr Med Khim.* 1998 January-February; 44(1):70–6; Ghiselli A. et al. New approaches for measuring plasma or serum antioxidant capacity: a methodological note. *Free Radic Biol Med.* 1994; 16(1):135–7; Miller N. J. et al. A new method for measuring antioxidant activity. *Biochem Soc Trans.* 1993; 21(2):95S, each of which is incorporated by reference herein in its entirety). In one embodiment, the level of antioxidants in the tissue, blood, serum, cells, plasma of a subject is increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

In another specific embodiment, the invention provides a method for reducing the level of adducts in a subject comprising administering to the subject a therapeutically effective amount or a prophylactically effective amount of one or more of the oral compositions and/or parenteral compositions of the invention. Methods for measuring the level of adducts are well known in the art (see, e.g., Helleberg H. et al. A new approach for measuring protein adducts from benzo[a]pyrene diolepoxide by high performance liquid chromatography/tandem mass spectrometry. *Rapid Commun Mass Spectrom.* 2000; 14(18):1644–53; Giese R. W. et al. Measuring DNA adducts by gas chromatography-electron capture-mass spectrometry: trace organic analysis. *Methods Enzymol.* 1996; 271:504–22; Strickland P. T. et al. Methodologies for measuring carcinogen adducts in humans. *Cancer Epidemiol Biomarkers Prev.* 1993; 2(6): 607–19, each of which is incorporated by reference herein in its entirety). In one embodiment, the level of adducts in the tissue, blood, serum, cells, plasma of a subject is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

5.3.2 Methods of Treating and Preventing Chronic Liver Disease, Chronic HCV Infection or NASH in a Subject Depending on the subject, the therapeutic and healthful benefits of the oral compositions and parenteral compositions of the present invention can range from reducing liver enzymes (e.g., alanine aminotransferase (ALT), aspartate aminotransferase (AST), alkaline phosphatase (ALP)), reducing viral load, improving liver histology (e.g., fibrosis, cirrhosis, necrosis), and/or improving the quality of life of a subject with chronic liver disease or disorder, chronic HCV infection or NASH.

In particular, the invention provides a method for normalizing the level of liver enzymes in a subject comprising administering to the subject a therapeutically effective amount or a prophylactically effective amount of one or more of the oral compositions and/or parenteral compositions of the invention. Liver enzymes include but are not limited to glutamic oxaloacetic transaminase or aspartate aminotransferase (AST), glutamic pyruvic transaminase or alanine aminotransferase (ALT), gamma-glutamyl transpeptidase (GGT), glutamic-oxaloacetic transaminase (GOT), glutamic-pyruvic transaminase (GPT), alkaline phosphatase, bilirubin, etc. Methods for measuring the level of liver enzymes are well known in the art (see, e.g., Jeong S. Y. et al. Sandwich ELISA for measurement of cytosolic aspartate aminotransferase in sera from patients with liver diseases. *Clin Chem.* 2003; 49(5):826–9; Choi S. et al. [Development of a method for the immunological measurement of aspartate aminotransferase with monoclonal antibodies] (in Korean). *Taehan Kan Hakhoe Chi.* 2003; 9(2): 135–44; Burin des Roziers N. et al. A microtiter plate assay for measurement of serum alanine aminotransferase in blood donors. *Transfusion.* 1995; 35(4):331–4, each of which is incorporated by reference herein in its entirety). In one embodiment, the level of one or more liver enzyme, preferably ALT or AST, or the total amount of liver enzyme is reduced by at least 1,000-fold, at least 900-fold, at least 800-fold, at least 700-fold, at least 600-fold, at least 500-fold, at least 400-fold, at least 300-fold, at least 200-fold, at least 100-fold, at least 50-fold, at least 25-fold, at least 10-fold, at least 5-fold, at least 1-fold, or at least 90%, at least 80%, at least 70%, at least 60%, at least 50%, at least 40%, at least 30%, at least 20%, or at least 10%.

The invention also provides a method for reducing the level of cirrhosis in a subject comprising administering to the subject a therapeutically effective amount or a prophylactically effective amount of one or more of the oral compositions and/or parenteral compositions of the invention. Cirrhosis is characterized pathologically by loss of the normal microscopic lobular architecture, with fibrosis and nodular regeneration. The term is sometimes used to refer to chronic interstitial inflammation of any organ. Methods for measuring the extent of cirrhosis are well known in the art (see, e.g., Xie M. et al. [A measurement of liver volume and its changes in post-hepatitic cirrhosis] (in Chinese). *Zhonghua Wai Ke Za Zhi.* 1994; 32(11):657–8; Zimmerer J. et al. [Diagnosis of alcohol-induced liver cirrhosis by indirect portal vein pressure measurement and liver venography] (in German). *Z Gastroenterol.* 1992; 30(4):255–61; Fernandez M. et al. [Liver cirrhosis and portal hypertension: non-invasive measurement of blood flow in the portal vein with Doppler-duplex] (in Spanish). *Rev Med Chil.* 1991; 119(5):524–9, each of which is incorporated by reference herein in its entirety). In one embodiment, the level of cirrhosis is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% in the subject. In a specific embodiment, cirrhosis is reversed by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% in the subject.

The invention also provides a method for reducing the level of fibrosis, lobular hepatitis and/or periportal bridging necrosis in a subject comprising administering to the subject a therapeutically effective amount or a prophylactically effective amount of one or more of the oral compositions and/or parenteral compositions of the invention. Methods for measuring liver histoligies such as changes in the extent of fibrosis, lobular hepatitis, and periportal bridging necrosis are well known in the art (see, e.g., Wright M. et al. Measurement and determinants of the natural history of liver fibrosis in hepatitis C virus infection: a cross sectional and longitudinal study. *Gut.* 2003; 52(4):574–9; Jimenez W. et al. Measurement of fibrosis in needle liver biopsies: evaluation of a calorimetric method. *Hepatology.* 1985; 5(5):815–8; Hu O. Y. et al. The influence of chronic lobular hepatitis on pharmacokinetics of cefoperazone—a novel galactose single-point method as a measure of residual liver function. *Biopharm Drug Dispos.* 1994; 15(7):563–76, each of which is incorporated by reference herein in its entirety). In a specific embodiment, the level of fibrosis, which is the formation of fibrous tissue, fibroid or fibrous degeneration, is reduced by at least 1,000-fold, at least 900-fold, at least 800-fold, at least 700-fold, at least 600-fold, at least 500-fold, at least 400-fold, at least 300-fold, at least 200-fold, at least 100-fold, at least 50-fold, at least 25-fold, at least 10-fold, at least 5-fold, at least 1-fold, or at least 90%, at least 80%, at least 70%, at least 60%, at least 50%, at least 40%, at least 30%, at least 20%, or at least 10%. In another specific embodiment, the level of lobular hepatitis, wherein foci of inflammatory cells are also present in the sinusoids of the lobule, is reduced by at least 1,000-fold, at least 900-fold, at least 800-fold, at least 700-fold, at least 600-fold, at least 500-fold, at least 400-fold, at least 300-fold, at least 200-fold, at least 100-fold, at least 50-fold, at least 25-fold, at least 10-fold, at least 5-fold, at least 1-fold, or at least 90%, at least 80%, at least 70%, at least 60%, at least 50%, at least 40%, at least 30%, at least 20%, or at least 10%. In yet another specific embodiment, the level of periportal bridging necrosis is reduced by at least 1,000-fold, at least 900-fold, at least 800-fold, at least 700-fold, at least 600-fold, at least 500-fold, at least 400-fold, at least 300-fold, at least 200-fold, at least 100-fold, at least 50-fold, at least 25-fold, at least 10-fold, at least 5-fold, at least 1-fold, or at least 90%, at least 80%, at least 70%, at least 60%, at least 50%, at least 40%, at least 30%, at least 20%, or at least 10%.

The invention further provides a method for improving the quality of life of a subject comprising administering to the subject a therapeutically effective amount or a prophylactically effective amount of one or more of the oral compositions and/or parenteral compositions of the invention. In one embodiment, the quality of life of a subject can be calculated using the RAND short-form 36 item survey (SF36). In certain embodiments, the quality of life of a subject which received a therapeutically effective amount or a prophylactically effective amount of one or more of the oral compositions and/or parenteral compositions of the invention shows reduced limitations in physical activities, reduced limitations in social activities, reduced limitations in usual role activities, reduced bodily pain, improved general mental health (e.g., psychological distress and well-being), improved vitality (e.g., energy and fatigue), and/or improved general health perceptions.

The invention is further defined by reference to the following examples.

6. EXAMPLE 1

The following example illustrates the healthful benefits of the oral compositions and parenteral compositions of the invention in an open labeled, non-randomized, one center clinical trial at the Liver Unit, Department of Medicine, Hadassah-Hebrew University Medical Center, Jerusalem, Israel. Liver enzymes, HCV-RNA levels, liver histology, and quality of life of the subjects were monitored.

6.1 Materials 6.1.1 Subjects 50 subjects were studied in the clinical trial. The subjects were recruited from patients who have chronic hepatitis C. Naive patients and patients who have been treated with interferon or interferon plus ribavirin, but who have failed to respond or who only responded partially, were also included. The patients were given an opportunity to read a consent form and have any of their questions answered prior to providing consent. Once patients who would like to participate have been identified, their medical histories were reviewed and a physical examination including neurological examination was given to determine eligibility for participation in the study. Further, the patients' blood pressure, pulse, temperature, body weight, and height were measured.

Patients must have met none of the exclusion criteria below in order to be eligible for participation in this clinical trial:

serum creatinine level is greater than 1.5 times the upper limit of normal at screening;

ongoing pregnancy or breast feeding;

history of hepatic, renal or other major organ transplantation;

evidence of alcohol or drug abuse;

history of having received any systemic anti-neoplastic or immunomodulatory treatment 6 months prior to the study;

decompensated liver disease as evidence by Childs B or C status;

inability to comply with the protocol;

HIV positive;

evidence of other causes of liver disease (e.g., hemochromatosis, Wilson's disease, autoimmune hepatitis, primary biliary cirrhosis, primary sclerosing cholangitis, alcoholic liver disease, chronic hepatitis B or D), or other severe debilitating diseases that would preclude the patient from participating in the study;

fulminant liver failure or severe deteriorating synthetic liver functions;

irreversible neurological deficit;

other major clinical conditions not related to the primary disease;

history of major psychiatric disturbance;

acute infectious disease; and fever from any cause.

Out of the 50 subjects selected, 29 were male and 21 were female. The mean age of the subjects was 53.5 years old (between 23 to 80 years old). All subjects were HCV RNA positive for more than 6 months and have been diagnosed with chronic active hepatitis. All subjects were negative for HBV, autoimmune markers, and HIV.

The subjects were required to abstain from alternative medications or vitamin supplements for three months prior to enrollment in the study. All subjects have had a liver biopsy performed within three years prior to enrollment in the study in order to determine that they have changes compatible with chronic hepatitis C. The subjects received treatment as described below.

The privacy of the subjects and all confidentiality issues were handled in accordance with the Hadassah University Hospital IRB guidelines.

6.1.2 Preparation of Oral Compositions

The following oral compositions were prepared:

(1) a first oral composition comprising two 250 mg capsules of glycyrrhizin (licorice extract 16%);

(2) a second oral composition comprising one 500 mg capsule of *schisandra* extract 30:1;

(3) a third oral composition comprising four 500 mg capsules of buffered ascorbic acid;

(4) a fourth oral composition comprising one 150 mg capsule of reduced L-glutathione;

(5) a fifth oral composition comprising one 250 mg capsule of milk thistle extract 80%;

(6) a sixth oral composition comprising one 150 mg capsule of lipoic acid;

(7) a seventh oral composition comprising two 400 iu capsules of d-alpha tocopherol (mixed);

The glycyrrhizin (250 mg capsules), *schisandra* extract 30:1 (500 mg capsules), buffered ascorbic acid (500 mg capsules), reduced L-glutathione (150 mg capsules), milk thistle extract 80% (250 mg capsules), lipoic acid (150 mg capsules), and mixed d-alpha tocopherol (400 iu capsules) used to prepare the oral compositions were obtained from Vital Nutrients (Middletown, Conn.).

6.1.3 Preparation of Parenteral Compositions

The following parenteral compositions were prepared:

(1) a first parenteral composition comprising 120 mg of glycyrrhizin;

(2) a second parenteral composition comprising 10,000 mg of ascorbic acid;

(3) a third parenteral composition comprising 750 mg of L-glutathione; and (4) a fourth parenteral composition comprising 1 ml of vitamin B-complex.

The glycyrrhizin, ascorbic acid, L-glutathione, and B-complex used to prepare the parenteral compositions were obtained from Vital Nutrients (Middletown, Conn.). The glycyrrhizin, ascorbic acid, L-glutathione, and vitamin B-complex were each mixed and added to 40 ml of sterile water or normal saline for infusion.

6.2 Experimental Design

Figure 1:
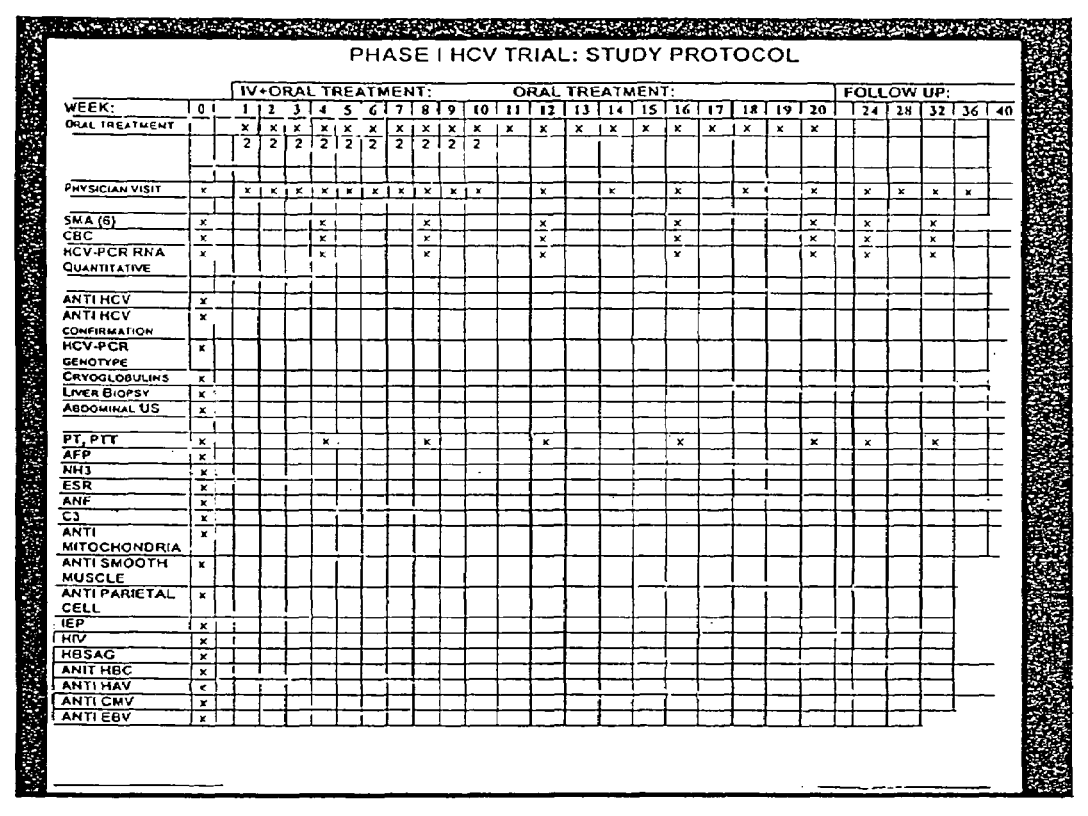

FIG. 1 shows the schedule of the clinical study. For the first twenty weeks of the study, the experimental subjects were given for oral administration the first oral composition, two times a day (a total of 1,000 mg of glycyrrhizin); the second oral composition, three times a day (a total of 1,500 mg of *schisandra* extract); the third oral composition, three times a day (a total of 6,000 mg of ascorbic acid); the fourth oral composition, two times a day (a total of 300 mg of L-glutathione); the fifth oral composition, three times a day (a total of 750 mg of milk thistle extract); the sixth oral composition, two times a day (a total of 300 mg of lipoic acid); and the seventh oral composition, one time a day (a total of 800 iu of d-alpha-tocopherol).

For the first ten weeks of the study, the experimental subjects were also given by intravenous (iv) injection two times a week the first parenteral composition, the second parenteral composition, the third parenteral composition, and the fourth parenteral composition. A large antecubital vein was selected for each subject and either a 20-gauge catheter or 21-gauge butterfly was used to gain venous access following aseptic preparations.

The subjects were not hospitalized and were followed for an additional twenty weeks following completion of the oral treatment at the Liver Unit Clinic or the Day Care Center at Hadassah, Israel. The subjects were asked to abstain from alcohol or the use of any antioxidants or alternative or complementary medications during the study period.

Blood samples (30 ml) of the subjects were obtained for routine liver chemistries (ALT, AST, ALP, albumin, total bilirubin), other general chemistries (glucose, sodium, potassium, chloride, free ammonia), and HCV genotype at the beginning of the treatment. An abdominal ultrasound was performed at the beginning of the treatment and liver biopsy was both performed before and after the completion of the treatment.

The subjects were monitored with a variety of safety, biologic, and efficacy parameters during the baseline, treatment, and post-treatment periods. The safety parameters included general clinical safety parameters to monitor the subject's overall status as well as specific organ systems. Individuals who suffered intercurrent exacerbation of the disease were removed from the study and treated by conventional clinical therapy.

The liver enzymes of each subject were measured weekly throughout the entire study.

The viral load of each subject was determined at week 10 (after completion of the iv treatment) and at week 20 (after completion of the oral treatment).

The liver histology of each subject was studied using the HAI scoring system (See FIG. 2). An HAI score is the combined scores for necrosis, inflammation, and fibrosis.

The quality of life of each subject was calculated using the RAND short-form 36 item survey (SF36) which was designed for use in clinical practice and research, health policy evaluations, and general population surveys. The SF36 includes one multi-item scale that assesses eight health concepts: 1) limitations in physical activities because of health problems; 2) limitations in social activities because of physical or emotional problems; 3) limitations in usual role activities because of physical health problems; 4) bodily pain; 5) general mental health (psychological distress and well-being); 6) limitations in usual role activities because of emotional problems; 7) vitality (energy and fatigue); and 8) general health perceptions.

6.3 Results

The HCV genotype distribution of the subjects is shown in Table 1 below.

TABLE 1

| HCV genotype | no. of patients |
| --- | --- |
| IA | 4 |
| IB | 28 |
| IA/IB | 1 |
| II | 8 |
| IIIA | 6 |
| IV | 3 |

The effects of the treatment on the liver enzymes, viral load, liver histology, and quality of life of the subjects are shown in Table 2 below.

TABLE 2

| | Reduced liver enzymes | Reduced viral load | Improved biopsy HAI score | Improved SF36 quality of life |
| --- | --- | --- | --- | --- |
| N | 20/49 | 12/49 | 17/38 | 26/45 |
| % | 40.8 | 24 | 45 | 57 |

6.3.1 Changes in Liver Enzymes

The changes in liver enzyme ALT of the subjects at week 0 (before treatment), week 6, week 10 (after iv treatment), week 20 (after oral treatment), and week 24 (post-treatment) are shown in FIG. 3. Specifically, the changes in liver enzymes ALT and AST of patient no. 124 are shown in FIG. 4, and the changes in liver enzyme ALT of patient no. 139 are shown in FIG. 5.

Out of the 50 subjects, 33 had an abnormal level of ALT before treatment. Table 3 shows the percentages of subjects whose liver enzyme(s) decreased by more than 25% after completion of the iv treatment (week 10), and after completion of the oral treatment (week 20).

TABLE 3

| | Week 10 | Week 20 |
| --- | --- | --- |
| All subjects (N = 50) | 46.0% | 40.8% |
| Subjects with abnormal ALT (N = 33) | 57.2% | 51.5% |

Table 4 shows the percentages of the 33 subjects with an abnormal level of ALT before treatment whose liver enzyme (s) normalized after completion of the iv treatment (week 10), and after completion of the oral treatment (week 20).

TABLE 4

| | Week 10 | Week 20 |
| --- | --- | --- |
| Subjects with abnormal ALT (N = 33) | 27.2% | 33.0% |

6.3.2 Changes in Viral Load

Table 5 shows the percentages of subjects whose viral load had a 1 log reduction after completion of the iv treatment (week 10), and after completion of the oral treatment (week 20).

TABLE 5

| | Week 10 | Week 20 |
| --- | --- | --- |
| 1 log reduction of viral load | 12.0% | 24.0% |

6.3.3 Changes in Liver Histology

Table 6 shows the percentages of subjects whose HAI biopsy score reduced by 2 points.

TABLE 6

| | Fibrosis | Lobular hepatitis | Periportal bridging necrosis | Total score |
| --- | --- | --- | --- | --- |
| Subjects with 2 point reduction in biopsy score | 5 13% | 7 18% | 7 18% | 17 45% |

The changes in liver biopsy of patient nos. 110 and 141 before (week 0) and after (week 20) treatment are shown in FIGS. 6 and 7, respectively.

6.3.4 Changes in Quality of Life

The changes in quality of life of the subjects (as determined by SF36) before (week 0) and after (week 20) treatment are shown in FIG. 8.

6.3.5 Adverse Events

No major adverse events were observed in the subjects. None of the subjects discontinued treatment. A few minor adverse events were reported as shown in Table 7 below.

TABLE 7

| Minor adverse event | No. of subjects affected |
| --- | --- |
| Alteration of bowel movements | 3 |
| Abdominal pains | 3 |
| Hypertension | 2 |
| Hypokalemia (mild) | 3 |

7. EXAMPLE 2

The following example describes the use of the oral compositions and/or parenteral compositions of the invention in subjects with a chronic liver disease.

7.1 Experimental Design A

For 20 weeks, the subjects are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day. The subjects are followed for 20 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

7.2 Experimental Design B

For 10 weeks, the subjects are intravenously injected with 120 mg glycyrrhizin, two times a week; 10,000 mg ascorbic acid, two times a week; 750 mg L-glutathione, two times a week; and 1 ml vitamin B-complex, two times a week. The subjects are followed for 10 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

7.3 Experimental Design C

For the first 10 weeks, the subjects are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day; and intravenously injected with 120 mg glycyrrhizin, two times a week; 10,000 mg ascorbic acid, two times a week; 750 mg L-glutathione, two times a week; and 1 ml vitamin B-complex, two times a week.

For week 11 to 20, the subjects are orally given 500 mg glycyrrhizin capsules, two times a day; 500 mg *schisandra* capsules, three times a day; 2,000 mg ascorbic acid capsules, three times a day; 150 mg L-glutathione capsules, two times a day; 250 mg silymarin capsule, three times a day; 150 mg lipoic acid capsules, two times a day; and 800 iu d-alpha tocopherol capsule, once a day. The subjects are followed for 20 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

8. EXAMPLE 3

The following example describes the use of the oral compositions and/or parenteral compositions of the invention in subjects with chronic HCV infection.

8.1 Experimental Design A

For 20 weeks, the subjects are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day. The subjects are followed for 20 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

8.2 Experimental Design B

For 10 weeks, the subjects are intravenously injected with 120 mg glycyrrhizin, two times a week; 10,000 mg ascorbic acid, two times a week; 750 mg L-glutathione, two times a week; and 1 ml vitamin B-complex, two times a week. The subjects are followed for 10 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

8.3 Experimental Design C

For the first 10 weeks, the subjects are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day; and intravenously injected with 120 mg glycyrrhizin, two times a week; 10,000 mg ascorbic acid, two times a week; 750 mg L-glutathione, two times a week; and 1 ml vitamin B-complex, two times a week.

For week 11 to 20, the subjects are orally given 500 mg glycyrrhizin capsules, two times a day; 500 mg *schisandra* capsules, three times a day; 2,000 mg ascorbic acid capsules, three times a day; 150 mg L-glutathione capsules, two times a day; 250 mg silymarin capsule, three times a day; 150 mg lipoic acid capsules, two times a day; and 800 iu d-alpha tocopherol capsule, once a day. The subjects are followed for 20 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

For 10 weeks, the subjects are intravenously injected with 120 mg glycyrrhizin, two times a week; 10,000 mg ascorbic acid, two times a week; 750 mg L-glutathione, two times a week; and 1 ml vitamin B-complex, two times a week. The subjects are followed for 10 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

9. EXAMPLE 4

The following example describes the use of the oral compositions and/or parenteral compositions of the invention in subjects with NASH.

9.1 Experimental Design A

For 20 weeks, the subjects are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day. The subjects are followed for 20 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

9.2 Experimental Design B

For 10 weeks, the subjects are intravenously injected with 120 mg glycyrrhizin, two times a week; 10,000 mg ascorbic acid, two times a week; 750 mg L-glutathione, two times a week; and 1 ml vitamin B-complex, two times a week. The subjects are followed for 10 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

9.3 Experimental Design C

For the first 10 weeks, the subjects are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day; and intravenously injected with 120 mg glycyrrhizin, two times a week; 10,000 mg ascorbic acid, two times a week; 750 mg L-glutathione, two times a week; and 1 ml vitamin B-complex, two times a week.

For week 11 to 20, the subjects are orally given 500 mg glycyrrhizin capsules, two times a day; 500 mg *schisandra* capsules, three times a day; 2,000 mg ascorbic acid capsules, three times a day; 150 mg L-glutathione capsules, two times a day; 250 mg silymarin capsule, three times a day; 150 mg lipoic acid capsules, two times a day; and 800 iu d-alpha tocopherol capsule, once a day. The subjects are followed for 20 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

For 10 weeks, the subjects are intravenously injected with 120 mg glycyrrhizin, two times a week; 10,000 mg ascorbic acid, two times a week; 750 mg L-glutathione, two times a week; and 1 ml vitamin B-complex, two times a week. The subjects are followed for 10 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

10. EXAMPLE 5

The following example describes the long-term use of the oral compositions and/or parenteral compositions of the invention.

10.1 Experimental Design A

For 6 months, the subjects are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day. The subjects are followed for 6 months after treatment.

Levels of free oxygen radicals, antioxidants, adducts, liver enzymes, and HCV-RNA, liver histology, and quality of life of the subjects before treatment, during treatment (weekly), and post-treatment are monitored.

10.2 Experimental Design B

For 3 months, the subjects are intravenously injected with 120 mg glycyrrhizin, two times a week; 10,000 mg ascorbic acid, two times a week; 750 mg L-glutathione, two times a week; and 1 ml vitamin B-complex, two times a week. The subjects are followed for 3 months after treatment.

Levels of free oxygen radicals, antioxidants, adducts, liver enzymes, and HCV-RNA, liver histology, and quality of life of the subjects before treatment, during treatment (weekly), and post-treatment are monitored.

10.3 Experimental Design C

For the first 3 months, the subjects are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day; and intravenously injected with 120 mg glycyrrhizin, two times a week; 10,000 mg ascorbic acid, two times a week; 750 mg L-glutathione, two times a week; and 1 ml vitamin B-complex, two times a week.

For months 4 to 6, the subjects are orally given 500 mg glycyrrhizin capsules, two times a day; 500 mg *schisandra* capsules, three times a day; 2,000 mg ascorbic acid capsules, three times a day; 150 mg L-glutathione capsules, two times a day; 250 mg silymarin capsule, three times a day; 150 mg lipoic acid capsules, two times a day; and 800 iu d-alpha tocopherol capsule, once a day. The subjects are followed for 6 months after treatment.

Levels of free oxygen radicals, antioxidants, adducts, liver enzymes, and HCV-RNA, liver histology, and quality of life of the subjects before treatment, during treatment (weekly), and post-treatment are monitored.

For 3 months, the subjects are intravenously injected with 120 mg glycyrrhizin, two times a week; 10,000 mg ascorbic acid, two times a week; 750 mg L-glutathione, two times a week; and 1 ml vitamin B-complex, two times a week. The subjects are followed for 3 months after treatment.

Levels of free oxygen radicals, antioxidants, adducts, liver enzymes, and HCV-RNA, liver histology, and quality of life of the subjects before treatment, during treatment (weekly), and post-treatment are monitored.

11. EXAMPLE 6

The following example illustrates the healthful benefits of the oral compositions and/or parenteral compositions of the invention administered together with oral vitamins, pegylated interferon, and/or ribavirin in anti-viral therapy.

11.1 Experimental Design A

For 20 weeks, four groups of subjects (Groups 1–4) are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day. Oral vitamins, pegylated interferon, and ribavin are also given to Group 2, Group 3, and Group 4, respectively. The subjects are followed for 20 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

11.2 Experimental Design B

For 10 weeks, four groups of subjects (Groups 1–4) are intravenously injected with 120 mg glycyrrhizin, two times a week; 10,000 mg ascorbic acid, two times a week; 750 mg L-glutathione, two times a week; and 1 ml vitamin B-complex, two times a week. Oral vitamins, pegylated interferon, and ribavin are also given to Group 2, Group 3, and Group 4, respectively. The subjects are followed for 10 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

11.3 Experimental Design C

For the first 10 weeks, four groups of subjects (Groups 1–4) are orally given two 250 mg glycyrrhizin capsules, two times a day; one 500 mg *schisandra* capsule, three times a day; four 500 mg ascorbic acid capsules, three times a day; one 150 mg L-glutathione capsule, two times a day; one 250 mg silymarin capsule, three times a day; one 150 mg lipoic acid capsule, two times a day; and two 400 iu d-alpha tocopherol capsules, once a day; and intravenously injected with 120 mg glycyrrhizin, two times a week; 10,000 mg ascorbic acid, two times a week; 750 mg L-glutathione, two times a week; and 1 ml vitamin B-complex, two times a week.

For week 11 to 20, the subjects are orally given 500 mg glycyrrhizin capsules, two times a day; 500 mg *schisandra* capsules, three times a day; 2,000 mg ascorbic acid capsules, three times a day; 150 mg L-glutathione capsules, two times a day; 250 mg silymarin capsule, three times a day; 150 mg lipoic acid capsules, two times a day; and 800 iu d-alpha tocopherol capsule, once a day.

Oral vitamins, pegylated interferon, and ribavin are also given to Group 2, Group 3, and Group 4, respectively. The subjects are followed for 20 weeks after treatment.

Levels of free oxygen radicals, antioxidants, adducts, liver enzymes, and HCV-RNA, liver histology, and quality of life of the subjects before treatment, during treatment (weekly), and post-treatment are monitored.

12. EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference in their entireties into the specification to the same extent as if each individual publication, patent or patent application was specifically and individually indicated to be incorporated herein by reference.

Citation or discussion of a reference herein shall not be construed as an admission that such is prior art to the present invention.

What is claimed is:

1. A composition comprising glycyrrhizin, *schisandra* extract, ascorbic acid, L-glutathione, silymarin, lipoic acid, and d-alpha-tocopherol in amounts together effective to treat chronic liver disease, chronic HCV infection, or NASH in a subject, wherein the amount of glycyrrhizin is in the range of 1,000 to 1,500 mg, the amount of *schisandra* extract is in the range of 1,500 to 3,000 mg, the amount of ascorbic acid is in the range of 500 to 10,000 mg, the amount of L-glutathione is in the range of 50 to 1,000 mg, the amount of silymarin is in the range of 80 to 1,000 mg, the amount of lipoic acid is in the range of 150 to 1,200 mg, and the amount of d-alpha-tocopherol is in the range of 200 to 1,600 iu.

2. The composition of claim 1 in capsule form.

3. The composition of claim 2, wherein the glycyrrhizin, *schisandra* extract, ascorbic acid, L-glutathione, silymarin, lipoic acid, and d-alpha-tocopherol are in amounts together effective to treat chronic HCV infection.

4. The composition of claim 1, wherein the glycyrrhizin, *schisandra* extract, ascorbic acid, L-glutathione, silymarin, lipoic acid, and d-alpha-tocopherol are in amounts together effective to treat chronic HCV infection.

5. A kit comprising a container comprising the composition of claim 1.

6. The kit of claim 5, wherein the composition comprises glycyrrhizin, *schisandra* extract, ascorbic acid, L-glutathione, silymarin, lipoic acid, and d-alpha-tocopherol in amounts together effective to treat chronic HCV infection.

7. A composition comprising glycyrrhizin, ascorbic acid, L-glutathione, and vitamin B-complex in amounts together effective to treat chronic liver disease, chronic HCV infection, or NASH in a subject, wherein the amount of glycyrrhizin is in the range of 10 to 500 mg, the amount of ascorbic acid is in the range of 1,000 to 20,000 mg, the amount of L-glutathione is in the range of 250 to 1,500 mg, and the amount of vitamin B-complex is in the range of 0.1 to 100 ml.

8. A syringe containing the composition of claim 7.

9. The composition of claim 8, wherein the glycyrrhizin, ascorbic acid, L-glutathione, and vitamin B-complex are in amounts together effective to treat chronic HCV infection.

10. The composition of claim 7, wherein the glycyrrhizin, ascorbic acid, L-glutathione, and vitamin B-complex are in amounts together effective to treat chronic HCV infection.

11. A kit comprising a container comprising the composition of claim 7.

12. The kit of claim 11, wherein the composition comprises glycyrrhizin, ascorbic acid, L-glutathione, and vitamin B-complex in amounts together effective to treat chronic HCV infection.

13. A method for treating chronic liver disease, chronic HCV infection or NASH in a subject comprising administering to the subject an amount of the composition of claim 1 effective to treat chronic liver disease, chronic HCV infection or NASH.

14. The method of claim 13, wherein the composition of claim 1 is administered to the subject orally.

15. The method of claim 14 for treating chronic HCV infection.

16. The method of claim 13 for treating chronic HCV infection.

17. A method for treating chronic liver disease, chronic HCV infection or NASH in a subject comprising administering to the subject an amount of the composition of claim 7 effective to treat chronic liver disease, chronic HCV infection or NASH.

18. The method of claim 17, wherein the composition of claim 7 is parenterally administered to the subject.

19. The method of claim 18 for treating chronic HCV infection.

20. The method of claim 17, wherein the composition of claim 7 is administered to the subject by infusion.

21. The method of claim 20 for treating chronic HCV infection.

22. The method of claim 17 for treating chronic HCV infection.

23. A method for treating chronic liver disease, chronic HCV infection or NASH in a subject comprising administering to the subject an amount of
   (a) a first composition comprising glycyrrhizin, *schisandra* extract, ascorbic acid, L-glutathione, silymarin, lipoic acid, and d-alpha-tocopherol, wherein the amount of glycyrrhizin is in the range of 1,000 to 1,500 mg, the amount of *schisandra* extract is in the range of 1,500 to 3,000 mg, the amount of ascorbic acid is in the range of 500 to 10,000 mg, the amount of L-glutathione is in the range of 50 to 1,000 mg, the amount of silymarin is in the range of 80 to 1,000 mg, the amount of lipoic acid is in the range of 150 to 1,200 mg, and the amount of d-alpha-tocopherol is in the range of 200 to 1,600 iu; and
   (b) a second composition comprising glycyrrhizin, ascorbic acid, L-glutathione, and vitamin B-complex, wherein the amount of glycyrrhizin is in the range of 10 to 500 mg, the amount of ascorbic acid is in the range of 1,000 to 20,000 mg, the amount of L-glutathione is in the range of 250 to 1,500 mg, and the amount of vitamin B-complex is in the range of 0.1 to 100 ml, said amount being effective to treat chronic liver disease, chronic HCV infection or NASH.

24. The method of claim 23, wherein the first composition is administered to the subject orally.

25. The method of claim 24 for treating chronic HCV infection.

26. The method of claim 23 or 24, wherein the second composition is parenterally administered to the subject.

27. The method of claim 26, wherein the second composition is administered to the subject by infusion.

28. The method of claim 27 for treating chronic HCV infection.

29. The method of claim 26 for treating chronic HCV infection.

30. The method of claim 23 for treating chronic HCV infection.

31. A method for treating chronic liver disease, chronic HCV infection or NASH in a subject comprising administering to the subject glycyrrhizin, *schisandra* extract, ascorbic acid, L-glutathione, silymarin, lipoic acid, and d-alpha-tocopherol, in amounts together effective to treat chronic liver disease, chronic HCV infection or NASH, wherein 1,000 to 1,500 mg of glycyrrhizin, 1,000 to 3,000 mg of *schisandra* extract, 50 to 10,000 mg of ascorbic acid, 50 to 1,000 mg of L-glutathione, 80 to 1,000 mg of silymarin, 100 to 1,200 mg of lipoic acid, and 200 to 1,600 iu of d-alpha-tocopherol are administered to said subject.

32. The method of claim 31 wherein the glycyrrhizin, *schisandra* extract, ascorbic acid, L-glutathione, silymarin, lipoic acid, and d-alpha-tocopherol are administered to the subject orally.

33. The method of claim 32 for treating chronic HCV infection.

34. The method of claim 31 for treating chronic HCV infection.

35. A method for treating chronic liver disease, chronic HCV infection or NASH in a subject comprising administering to the subject glycyrrhizin, ascorbic acid, L-glutathione, and vitamin B-complex, in amounts together effective to treat chronic liver disease, chronic HCV infection or NASH, wherein 10 to 500 mg of glycyrrhizin, 1,000 to 20,000 mg of ascorbic acid, 250 to 1,500 mg of L-glutathione, and 0.1 to 100 ml of vitamin B-complex are administered to said subject.

36. The method of claim 35 wherein the glycyrrhizin, ascorbic acid, L-glutathione, and vitamin B-complex are parenterally administered to the subject.

37. The method of claim 36 for treating chronic HCV infection.

38. The method of claim 36, wherein the glycyrrhizin, ascorbic acid, L-glutathione, and vitamin B-complex are administered to the subject by infusion.

39. The method of claim 38 for treating chronic HCV infection.

40. The method of claim 35 for treating chronic HCV infection.

41. A method for treating chronic liver disease, chronic HCV infection or NASH in a subject comprising:
(a) administering to the subject orally each day for 20 weeks:
  (i) 1,000 to 1,500 mg of glycyrrhizin;
  (ii) 1,500 to 3,000 mg of *schisandra* extract;
  (iii) 500 to 10,000 mg of ascorbic acid;
  (iv) 50 to 1,000 mg of L-glutathione;
  (v) 80 to 1,000 mg of silymarin;
  (vi) 150 to 1,200 mg of lipoic acid
  (vii) 200 to 1,600 i,u, of d-alpha-tocopherol; and
(b) parenterally administering to the subject twice a week for 10 weeks:
  (i) 10 to 500 mg of glycyrrhizin;
  (ii) 1,000 to 20,000 mg of ascorbic acid;
  (iii) 250 to 1,500 mg of L-glutathione; and
  (iv) 0,1 to 100 ml of vitamin B-complex.

42. The method of claim 41, wherein the level of free oxygen radicals in the subject is reduced.

43. The method of claim 41, wherein the level of antioxidants in the subject is increased.

44. The method of claim 41, wherein the level of adducts in the subject is reduced.

45. The method of claim 41, wherein the level of liver enzymes in the subject is normalized.

46. The method of claim 41, wherein the level of cirrhosis in the subject is reduced.

47. The method of claim 41, wherein the level of fibrosis, lobular hepatitis or periportal bridging necrosis in the subject is reduced.

48. The method of claim 41 for treating chronic HCV infection.

49. A kit comprising:
(a) a first container comprising a first composition comprising glycyrrhizin, *schisandra* extract, ascorbic acid, L-glutathione, silymarin, lipoic acid, and d-alpha-tocopherol, in amounts together effective to treat chronic liver disease, chronic HCV infection or NASH, wherein the amount of glycyrrhizin is in the range of 1,000 to 1,500 mg, the amount of *schisandra* extract is in the range of 1,500 to 3,000 mg, the amount of ascorbic acid is in the range of 500 to 10,000 mg, the amount of L-glutathione is in the range of 50 to 1,000 mg, the amount of silymarin is in the range of 80 to 1,000 mg, the amount of lipoic acid is in the range of 150 to 1,200 mg, and the amount of d-alpha-tocopherol is in the range of 200 to 1,600 iu; and
(b) a second container comprising a second composition comprising glycyrrhizin, ascorbic acid, L-glutathione, and vitamin B-complex, in amounts together effective to treat chronic liver disease, chronic HCV infection or NASH, wherein the amount of glycyrrhizin is in the range of 10 to 500 mg, the amount of ascorbic acid is in the range of 1,000 to 20,000 mg, the amount of L-glutathione is in the range of 250 to 1,500 mg, and the amount of vitamin B-complex is in the range of 0,1 to 100 ml.

50. The kit of claim 49, wherein the second container is a syringe.

51. The kit of claim 50, wherein the first composition of the first container comprises glycyrrhizin, *schisandra* extract, ascorbic acid, L-glutathione, silymarin, lipoic acid, and d-alpha-tocopherol in amounts together effective to treat chronic HCV infection, and wherein the second composition of the second container comprises glycyrrhizin, ascorbic acid, L-glutathione, and vitamin B-complex in amounts together effective to treat chronic HCV infection.

52. The kit of claim 49, wherein the first composition of the first container comprises glycyrrhizin, *schisandra* extract, ascorbic acid, L-glutathione, silymarin, lipoic acid, and d-alpha-tocopherol in amounts together effective to treat chronic HCV infection, and wherein the second composition of the second container comprises glycyrrhizin, ascorbic acid, L-glutathione, and vitamin B-complex in amounts together effective to treat chronic HCV infection.

* * * * *